(12) United States Patent
Storm et al.

(10) Patent No.: US 7,276,345 B2
(45) Date of Patent: Oct. 2, 2007

(54) METHOD FOR IDENTIFYING CANDIDATE COMPOUNDS THAT BIND TO A HUMAN TYPE IX ADENYLYL CYCLASE POLYPEPTIDES

(75) Inventors: Daniel R. Storm, Brier, WA (US); Beth Hacker, Seattle, WA (US); James E. Tomlinson, Burlingame, CA (US)

(73) Assignees: Millennium Pharmaceuticals, Inc., Cambridge, MA (US); University of Washington, Seattle, WA (US)

( * ) Notice: Subject to any disclaimer, the term of this patent is extended or adjusted under 35 U.S.C. 154(b) by 0 days.

(21) Appl. No.: 10/896,552

(22) Filed: Jul. 22, 2004

(65) Prior Publication Data

US 2005/0019809 A1    Jan. 27, 2005

Related U.S. Application Data

(60) Division of application No. 10/071,223, filed on Feb. 11, 2002, now Pat. No. 6,841,372, which is a division of application No. 09/473,717, filed on Dec. 29, 1999, now Pat. No. 6,372,475, which is a continuation of application No. PCT/US98/13541, filed on Jul. 1, 1998.

(60) Provisional application No. 60/098,559, filed on Jul. 1, 1997.

(51) Int. Cl.
G01N 33/53 (2006.01)
C12N 9/88 (2006.01)

(52) U.S. Cl. ........................................ 435/7.1; 435/232
(58) Field of Classification Search .................... None
See application file for complete search history.

(56) References Cited

U.S. PATENT DOCUMENTS 6,096,705 A * 8/2000 Lefkowitz et al. ............. 514/2

6,372,475 B1    4/2002 Storm et al.
6,841,372 B2    1/2005 Storm et al.
2002/0137174 A1    9/2002 Storm et al.

FOREIGN PATENT DOCUMENTS

WO    WO95/30012    11/1995
WO    WO96/25502    8/1996
WO    PCT/US98/13541    1/1999

OTHER PUBLICATIONS

Witkowski et al. (1999) Biochemistry 38:11643-11650.*
"Introduction to Protein Structure", Branden and Tooze, Garland Publishing Inc., New York, 1991, p. 247.*
Small et al., Pharmacogenetics 13:535-541, 2003.*
Defer et al., "Molecular cloning of the human type VIII adenylyl cyclase," FEBS Letters 351:109-113, 1994.
Ishikawa et al., "Isolation and characterization of a novel cardiac adenylyl cyclase cDNA," Jour. Biol. Chem. 267(19):13553-13557, 1992.
Nomura et al.., "Prediction of the coding sequences of unidentified human genes. I. The coding sequences of 40 new genes (KIAA0001-KIAA0040) deduced by analysis of randomly sampled cDNA clones from human immature myeloid cell line KG-1," DNA Research 1(1):27-35, 1994.
Stengel et al., "Different chromosomal localization of two adenylyl cyclase genes expressed in human brain," Hum. Genet. 90:126-130, 1992.
Hacker et al., "Cloning, chromosomal mapping and regulatory properties of the human type 9 adenylyl cyclase (ADCY9)," Genomics 50(1):97-104, 1998.
Premont et al., "Identification and characterization of a widely expressed form of adenylyl cyclase," Jour. Biol. Chem. 271(23);13900-13907, 1996.

* cited by examiner

*Primary Examiner*—David J. Steadman
(74) *Attorney, Agent, or Firm*—Cooley Godward Kronish, LLP

(57) ABSTRACT

The invention relates to novel human adenylyl cyclase nucleic acid and amino acid sequences. Also provided are vectors, host cells, recombinant methods for making and using the novel molecules and methods for identifying compounds which bind to the adenylyl cyclase proteins.

7 Claims, 15 Drawing Sheets

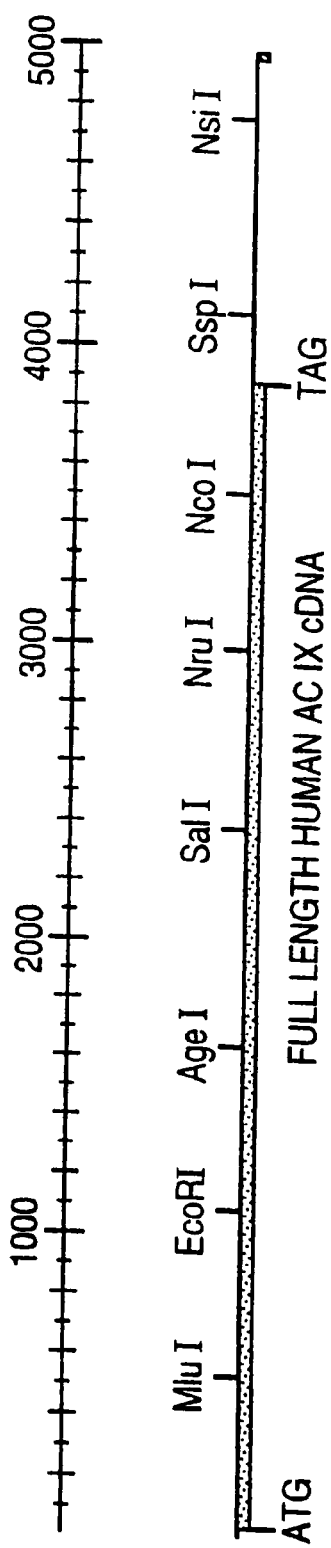
FIG. 1A
FIG. 1B
FIG. 1C

FIG. 2A

| | |
|---|---|
| CCCGGGACTC GACAACATGG CTTCCCCGCC CCACCAGCAG CTGCTGCATC<br>                   M  A  S  P  P  H  Q  Q  L  L  H  H | 50 |
| ACCACAGCAC CGAGGTGAGC TGCGACTCCA GGGGGACAG CAACAGCGTG<br>H  S  T  E  V  S  C  D  S  S  G  D  S  N  S  V | 100 |
| CGCGTCAAGA TCAACCCCAA GCAGCTGTCC TCCAACAGCC ACCCCAAGCA<br>R  V  K  I  N  P  K  Q  L  S  S  N  S  H  P  K  H | 150 |
| CTGCAAATAC AGCATCTCCT CTAGCTGCAG CAGCTCTGGG GACTCCGGG<br>C  K  Y  S  I  S  S    S  C  S    S  S  G    D  S  G  G | 200 |
| GCGTCCCCG GCGAGTGGGC GGCGGAGGCC GGCTGCGCAG GCAGAAGAAG<br>V  P  R    R  V  G    G  G  R    L  R  R    Q  K  K | 250 |
| CTGCCCCAGC TGTTCGAGAG GGCCTCCAGC CGCTGGTGGG ACCCCAAGTT<br>L  P  Q  L    F  E  R    A  S  S    R  W  W    D  P  K  F | 300 |
| CGACTCGGTG AACCTGGAGG AGGCCTGCCT GGAGCGCTGC TTCCCGCAGA<br>D  S  V    N  L  E    E  A  C    L  E  R    C    F  P  Q  T | 350 |
| CCCAGCGCCG GTTCCGGTAT GCGCTCTTCT ACATCGGCTT CGCCTGCCTT<br>Q  R  R    F  R  Y    A  L  F  Y    I  G  F    A  C  L | 400 |
| CTGTGGAGCA TCTATTTTGC GGTCCACATG AGATCCAGAC TGATCGTCAT<br>L  W  S  I    Y  F  A    V  H  M    R  S  R    L    I  V  M | 450 |
| GGTCGCCCCC GCGCTGTGCT TCCTCCTGGT GTGTGTGGGC TTCTTTCTGT<br>V  A  P    A  L  C    F  L  L  V    C  V  G    F  F  L  F | 500 |
| TTACCTTCAC CAAGCTGTAC GCCCGGCATT ACGCGTGGAC CTCGCTGGCT<br>T  F  T    K  L  Y    A  R  H  Y    A  W  T    S  L  A | 550 |
| CTCACCCTGC TGGTGTTCGC CCTGACCCTG GCTGCGCAGT TCCAGGTCTT<br>L  T  L  L    V  F  A    L  T  L    A  A  Q    F  Q  V  L | 600 |

FIG. 2B

```
GACGCCTGTC TCAGGACGCG GCGACAGCTC CAACCTTACG GCCACAGCCC   650
 T  P  V   S  G  R     D  S  S   N  L  T    A  T  A  R

GGCCCACAGA TACTTGCTTA TCTCAAGTGG GGAGCTTCTC CATGTGCATC   700
 P  T  D   T  C  L    S  Q  V  G  G  A  S  S  C  A  S
(P  T  D    T  C  L   S  Q  V  G   S  F  S   M  C  I)

GAAGTGCTCT TTTTGCTCTA TACCGTCATG CACTTACCTT TGTACCTGAG   750
 E  V  L  F  L  L  Y  T  V  M    H  L  P  L    Y  L  S

TTTGTGTCTG GGGGTGGCCT ACTCTGTCCT TTTGAGACC  TTTGGCTACC   800
 L  C  L    G  V  A  Y  S  V  L   F  E  T    F  G  Y  H

ATTTCCGGGA TGAAGCCTGC TTCCCCTCGC CCGGAGCCGG GGCCCTGCAC   850
 F  R  D   E  A  C    F  P  S  P   G  A  G   A  L  H

TGGGAGCTGC TGAGCAGGGG GCTGCTCCAC GGCTGCATCC ACGCCATCGG   900
 W  E  L  L   S  R  G    L  L  H   G  C  I  H  A  I  G

GGTCCACCTG TTCGTCATGT CCCAGGTGAG GTCCAGGAGC ACCTTCCTCA   950
 V  H  L    F  V  M  S   Q  V  R   S  R  S   T  F  L  K

AGGTGGGGCA ATCCATTATG CACGGGAAGG ACCTGGAAGT GGAAAAAGCC  1000
 V  G  Q   S  I  M    H  G  K  D   L  E  V   E  K  A

CTCAAAGAGA GGATGATTCA TTCCGTGATG CCAAGAATCA TAGCCGATGA  1050
 L  K  E  R   M  I  H   S  V  M   P  R  I  I   A  D  D

CTTAATGAAG CAGGGAGATG AGGAGAGTGA GAATTCTGTC AAGAGGCATG  1100
 L  M  K    Q  G  D  E    E  S  E   N  S  V  K  R  H  A

CCACCTCGAG CCCCAAGAAC AGGAAGAAAA AGTCTTCCAT CCAAAAAGCT  1150
 T  S  S    P  K  N    R  K  K  K  S  S  I    Q  K  A

CCTATAGCCT TCCGCCCTTT TAAGATGCAG CAGATCGAAG AAGTCAGTAT  1200
 P  I  A  F  R  P  F   K  M  Q    Q  I  E  E    V  S  I
```

FIG. 2C

```
TTTATTTGCA GATATCGTGG GCTTCACCAA GATGAGTGCC AACAAGTCTG    1250
 L  F  A  D  I  V  G  F  T  K  M  S  A  N  K  S  A

CCCACGCCCT GGTGGGTCTC CTGAACGATC TGTTCGGTCG CTTCGACCGC    1300
 H  A  L  V  G  L  L  N  D  L  F  G  R  F  D  R

CTGTGTGAGG AGACCAAGTG TGAGAAAATC AGCACCCTGG GAGACTGTTA    1350
 L  C  E  E  T  K  C  E  K  I  S  T  L  G  D  C  Y

CTACTGCGTG GCGGGCTGTC CCGAGCCCCG GGCCGACCAT GCCTACTGCT    1400
 Y  C  V  A  G  C  P  E  P  R  A  D  H  A  Y  C  C

GCATCGAGAT GGGCCTGGGC ATGATCAAGG CCATCGAGCA GTTCTGCCAG    1450
 I  E  M  G  L  G  M  I  K  A  I  E  Q  F  C  Q

GAGAAGAAGG AGATGGTGAA CATGAGAGTC GGGGTGCACA CGGGCACCGT    1500
 E  K  K  E  M  V  N  M  R  V  G  V  H  T  G  T  V

CCTTTGCGGC ATCCTGGGCA TGAGGAGGTT TAAATTTGAC GTGTGGTCCA    1550
 L  C  G  I  L  G  M  R  R  F  K  F  D  V  W  S  N

ACGATGTGAA CCTGGCCAAT CTCATGGAGC AGCTGGGAGT GGCCGGCAAA    1600
 D  V  N  L  A  N  L  M  E  Q  L  G  V  A  G  K

GTTCACATTT CTGAGGCCAC CGCAAAATAC TTAGATGACC GGTACGAAAT    1650
 V  H  I  S  E  A  T  A  K  Y  L  D  D  R  Y  E  M

GGAAGATGGG AAAGTTATTG AACGGCTGGG CCAGAGCGTG GTTGCTGACC    1700
 E  D  G  K  V  I  E  R  L  G  Q  S  V  V  A  D  Q

AGTTGAAAGG TTTGAAGACA TACCTGATAT CGGGTCAGAG AGCCAAGGAG    1750
 L  K  G  L  K  T  Y  L  I  S  G  Q  R  A  K  E

TCTCGCTGCA GCTGTGCAGA GGCCTTGCTT TCTGGCTTTG AGGTCATTGA    1800
 S  R  C  S  C  A  E  A  L  L  S  G  F  E  V  I  D
```

FIG. 2D

```
CGGCTCACAG GTGTCCTCAG GCCCTAGGGG ACAGGGGACA GGGTCATCAG    1850
 G  S  Q   V  S  S  G   P  R  G    Q  G  T    A  S  S  G

GGAATGTCAG TGACTTGGCG CAGACTGTCA AAACCTTTGA TAACCTTAAG    1900
 N  V  S   D  L  A    Q  T  V  K   T  F  D   N  L  K

ACCTGCCCTT CGTGCGGAAT CACATTTGCT CCCAAATCTG AAGCCGGCGC    1950
 T  C  P  S   C  G  I   T  F  A    P  K  S  E   A  G  A

CGAGGGAGGA GCACCTCAAA ACGGCTGCCA AGACGAGCAT AAAAACAGCA    2000
 E  G  G    A  P  Q  N   G  C  Q   D  E  H   K  N  S  T

CCAAGGCTTC TGGAGGACCT AATCCCAAAA CTCAGAACGG GCTCCTCAGC    2050
 K  A  S    G  G  P    N  P  K     T  Q  N  G   L  L  S

CCTCCCCAAG AGGAGAAGCT CACCAACAGT CAGACTTCTC TGTGTGAGAT    2100
 P  P  Q  E   E  K  L   T  N  S   Q  T  S  L   C  E  I

CTTGCAGGAG AAGGGAAGGT GGGCAGGGGT GAGCCTGGAC CAGTCGGCTC    2150
 L  Q  E    K  G  R  W   A  G  V   S  L  D   Q  S  A  L

TCCTTCCGCT GAGGTTCAAG AACATCCGGG AGAAAACGGA CGCCCACTTT    2200
 L  P  L    R  F  K    N  I  R  E   K  T  D   A  H  F

GTGGACGTTA TCAAAGAAGA CAGCCTGATG AAAGATTACT TTTTTAAGCC    2250
 V  D  V  I   K  E  D   S  L  M    K  D  Y  F   F  K  P

GCCCATTAAT CAGTTCAGCC TGAACTTCCT GGATCAGGAG CTGGAGCGAT    2300
 P  I  N    Q  F  S  L   N  F  L   D  Q  E    L  E  R  S

CCTACAGGAC CAGCTATCAG GAAGAGGTCA TAAAGAACTC CCCCGTGAAG    2350
 Y  R  T    S  Y  Q    E  E  V  I   K  N  S   P  V  K

ACGTTTGCTA GTCCCACCTT CAGCTCCCTC CTGGATGTGT TTCTGTCGAC    2400
 T  F  A  S   P  T  F   S  S  L    L  D  V  F   L  S  T
```

FIG. 2E

```
CACAGTGTTT CTGACGCTGT CCACCACCTG CTTCCTGAAG TACGAGGCGG    2450
 T  V  F    L  T  L  S    T  T  C    F  L  K    Y  E  A  A

CCACCGTGCC TCCCCCGCCC GCCGCCCTGG CGGTCTTCAG TGCAGCCCTG    2500
 T  V  P    P  P  P    A  A  L    A  V  F  S    A  A  L

CTGCTGGAGG TGCTGTCCCT CGCGGTGTCC ATCAGGATGG TGTTCTTCCT    2550
 L  L  E  V  L  S  L    A  V  S   I  R  M  V    F  F  L

GGAGGACGTC ATGGCCTGCA CCAAGCGCCT GCTGGAGTGG ATCGCCGGCT    2600
 E  D  V    M  A  C  T    K  R  L    L  E  W    I  A  G  W

GGCTACCACG TCACTGCATC GGGGCCATCC TGGTGTCGCT TCCCGCACTG    2650
 L  P  R    H  C  I    G  A  I  L    V  S  L    P  A  L

GCCGTCTACT CCCATGTCAC CTCCGAATAT GAGACCAACA TACACTTCCC    2700
 A  V  Y  S   H  V  T    S  E  Y    E  T  N  I   H  F  P

AGTGTTCACA GGCTCGGCCG CACTGATTGC CGTCGTGCAC TACTGTAACT    2750
 V  F  T    G  S  A  A    L  I  A    V  V  H    Y  C  N  F

TCTGCCAGCT CAGCTCCTGG ATGAGGTCCT CCCTCGCCAC CGTCGTGGGG    2800
 C  Q  L    S  S  W    M  R  S  S    L  A  T    V  V  G

GCCGGGCCGC TGCTCCTGCT CTACGTCTCC CTGTGCCCAG ACAGTTCTGT    2850
 A  G  P  L   L  L    Y  V  S    L  C  P  D    S  S  V

ATTAACTTCG CCCCTTGACG CAGTACAGAA TTTCAGTTCC GAGAGGAACC    2900
 L  T  S    P  L  D  A    V  Q  N    F  S  S    E  R  N  P

CGTGCAATAG TTCGGTGCCG CGTGACCTCC GGCGGCCCGC CAGCCTCATC    2950
 C  N  S    S  V  P    R  D  L  R    R  P  A  S  L  I

GGCCAGGAGG TGGTTCTCGT CTTCTTTCTC CTGCTCTTGT TGGTCTGGTT    3000
 G  Q  E  V   V  L  V    F  F  L    L  L  L  V   W  F
```

FIG. 2F

```
CCTGAATCGC GAATTTGAAG TCAGCTACCG CCTCCACTAC CACGGAGACG    3050
 L  N  R    E  F  E  V    S  Y  R    L  H  Y    H  G  D  V

TGGAAGCGGA TCTTCACCGC ACCAAGATCC AGAGCATGCG GGACCAGGCA    3100
 E  A  D    L  H  R    T  K  I  Q    S  M  R    D  Q  A

GACTGGCTGC TGAGGAACAT CATCCCCTAC CACGTGGCTG AGCAGCTGAA    3150
 D  W  L  L    R  N  I    I  P  Y    H  V  A  E    Q  L  K

GGTGTCCCAG ACCTACTCCA AGAACCACGA CAGCGGAGGG GTGATCTTCG    3200
 V  S  Q    T  Y  S  K    N  H  D    S  G  G    V  I  F  A

CCAGCATCGT CAACTTCAGC GAGTTCTACG AGGAGAACTA CGAGGGCGGC    3250
  S  I  V   N  F  S    E  F  Y  E    E  N  Y    E  G  G

AAGGAGTGCT ACCGGGTCCT CAACGAGCTC ATCGGGGACT TTGACGAGCT    3300
 K  E  C  Y    R  V  L    N  E  L    I  G  D  F    D  E  L

CCTAAGCAAG CCGGACTACA GCAGCATCGA GAAGATCAAG ACCATCGGAG    3350
 L  S  K    P  D  Y  S    S  I  E    K  I  K    T  I  G  A

CCACGTACAT GGCGGCGTCA GGGCTGAACA CCGCGCAGGC CCAGGACGGC    3400
  T  Y  M   A  A  S    G  L  N  T    A  Q  A    Q  D  G

AGCCACCCGC AGGAGCACCT GCAGATCCTG TTCGAGTTCG CCAAGGAGAT    3450
 S  H  P  Q    E  H  L    Q  I  L    F  E  F  A    K  E  M

GATGCGCGTG GTGGACGACT TCAACAACAA CATGCTGTGG TTCAACTTCA    3500
 M  R  V    V  D  D  F    N  N  N    M  L  W    F  N  F  K

AGCTCCGCGT CGGCTTCAAC CATGGCCCC TCACGGCCGG GGTCATCGGC    3550
 L  R  V    G  F  N    H  G  P  L    T  A  G    V  I  G

ACCACCAAGC TGCTGTACGA CATCTGGGGA GACACCGTCA ACATCGCCAG    3600
  T  T  K   L  L  Y  D    I  W  G    D  T  V  N    I  A  S
```

FIG. 2G

```
CAGGATGGAC ACCACCGGCG TGGAGTGCCG CATCCAGGTG AGCGAAGAGA    3650
 R  M  D    T  T  G    V  E  C  R   I  Q  V    S  E  E  S

GCTACCGCGT CTTGAGCAAG ATGGGCTATG ACTTCGACTA CAGAGGGACC    3700
 Y  R  V    L  S  K    M  G  Y    D  F  D  Y   R  G  T

GTGAATGTCA AGGGGAAAGG CCAGATGAAG ACCTACCTGT ACCCAAAGTG    3750
 V  N  V  K   G  K  G   Q  M  K    T  Y  L    Y  P  K  C

CACGGATCAC AGGGTCATCC CAGCACCAGC TGTCCATCTC CCCAGACATC    3800
 T  D  H    R  V  I  P   A  P  A   V  H  L    P  R  H  P

CGCGTCCAGG TGGATGGCAG CATCGGACGG TCTCCCACAG ACGAGATTGC    3850
 R  P  G    G  W  Q    H  R  T  V   S  H  R    R  D  C

CAACCTGGTG CCTTCTGTCC AGTATGTGGA CAAGACATCT CTGGGTTCTG    3900
 Q  P  G    A  F  C  P   V  C  G    Q  D  I  S   G  F

ACAGCAGCAC GCAGGCCAAG GATGCCCACC TGTCCCCAA GAGACCGTGG    3950

AAGGAGCCCG TCAAAGCCGA AGAAAGGGGT CGATTTGGCA AAGCCATAGA    4000

GAAAGACGAC TGTGACGAAA CAGGAATAGA AGAAGCCAAC GAACTCACCA    4050

AGCTCAACGT TTCAAAGAGT GTGTGAGGCG GCGCCCACCC GCTGCCCGAG    4100

GTGCTCTGTT TGTCGAAACA CAGTAATATT TGTATTTGGC TGTTGTGCTT    4150

TCCAAGCGCC ACAGTTGCCC TCCCCGGACG TGGTGTTATG TGGTCATTTC    4200
```

FIG. 2H

```
AGCCCTAACT TCTGTGTGGA TCACAGTTAT TCAGGGTTCA TTTTCATCCA    4250

TTCTTCCCTT TGCTCCCTT CCCTGGAAAC CCCGCTGCCT CTGGGTCATC     4300

CGTTCAGCAC GTGGTGGAGA ACAAGTGCCT TCAGGGCTGG CCTCGGCCTC    4350

GAGTCTGGG ACAGAGGCCG CCAGTGGAGA TCATGGCTTT GGGTATTATT     4400

TGACTTTTAG AACAAAAGCT GTGGTTAAGA TCTCATTTTT ATTGCTTTTT    4450

CCCACGTCCC ACGAGACACT ATTTTCGGTT CTCTGGCTAA TACCCTGTTT    4500

TTGAGTTTAT TTGTTTCTG TCTATGTCAC AGTGTCCCCC TACGACCCGA     4550

CCTCTCTATG TAAGCACACA TGGGCACACA CACTTGCATT CATGAATCTG    4600

ATATAAAGTG CCAGTAATCC GCCAAGAGGG GGTGCGAAGG GGGCATGTCA    4650

CGACAGCTCC GCCACCCCCC ATTGCCCACC CGCACTTTCC CGAGCACCGC    4700

GCCCCGTGGG CTGTCGGTGA GCCGCGCTCC CTGCACTGAG CGGGTTTAGG    4750

GGCTCGCCCA CATGCATGCA GGCCAAGACA GCAAATGCCA GCCGGGCACG    4800
```

FIG. 21

```
ACGCCTGTGT GCCCAGGCCT CGGGGGTCTC AGAGCCGCCT CTCACCCCCG     4850

ACCCTCCACC CAGGGGTCTC CCCGTCGGA GTGGAGGCGT TGGTCCTGGA     4900

AGCTGACTCA TCGGAGAGGG AAATACCAAA TAAACATCCG AGGTTGCAAA    4950

AAAAAAAAAA AAAAAAAAA AAAAAAAAAA AAAAA                    4985
```

FIG. 3A

```
Human IX   MASPHQQLL HHHSTEVSCD SSGDSNSVRV KINPKQLSSN HIPKHCKYSI  50
Mouse IX   MASPHQQLL HHHSTEVSCD SSGDSNSVRV KINPKQLSSN HIPKHCKYSI  50

Human IX   SSSCSSSSGDS GGMPRRVGGG GRLRRQKKLP QLFERASSRW WDPKFDSMNL  100
Mouse IX   SSSCSSSSGDS GG PRRVGGG GRLRRQKKLP QLFERASSRW WDPKFDSMNL  100

Human IX   EEACLERCFP QTQRRFRYAL FYIGFACLLW SIYFAVHMFS RLTVMVPAI   150
Mouse IX   EEACLERCFP QTQRRFRYAL FYMGFACLLW SIYFAVHMKS KVIVMVPAI   150

Human IX   CFL VCVGFF LFTFTKLYAR HYAWTSLALT LLVFALTLAA QFQVT TPMSG  200
Mouse IX   CFL VCVGFF LFTFTKLYAR HYAWTSLALT LLVFALTLAA QFQVW TP SG   200

Human IX   RQDSSN THT AHP DTCLSQ VGSFSM CIEV LFLLYTVMHL PLYLSLLGV    250
Mouse IX   RMDSSN HT  AHPADTCLSQ VGSFSH CIEV LLLYTVMQL PLYLSLFLGV  250

Human IX   AYSVLFETFG YHFRL EP CFP SPGGALHWE LLSR GLLHHC IHAIGMHLFV  300
Mouse IX   VYSVLFETFG YHFRNEI CMP SPGFGALHWE LLSRALLHMC IHAIGIHLFV  300

Human IX   MSQVRSRSTF LKVGQSIMHG KDLEVEKALK ERMIHSVMPR IIADDLMKQG   350
Mouse IX   MSQVRSRSTF LKVGQSIMHG KDLEVEKALK ERMIHSVMPR IIADDLMKQG   350
```

FIG. 3B

| | | |
|---|---|---|
| Human IX | DEESENSVKR HATSSPKNRK KKSSIQKAPI AFRPFKMQQI EEVSILFADI | 400 |
| Mouse IX | DEESENSVKR HATSSPKNRK KKSSIQKAPI AFRPFKMQQI EEVSILFADI | 400 |
| Human IX | VGFTKMSANK SAHALVGLLN DLFGRFDRLC E TKCEKIST LGDCYCVAG | 450 |
| Mouse IX | VGFTKMSANK SAHALVGLLN DLFGRFDRLC E TKCEKIST LGDCYCVAG | 450 |
| Human IX | CPEPRADHAY CCIEMGLGMI KAIEQFCQEK KEMVNMRVGV HTGTVLCGIL | 500 |
| Mouse IX | CPEPRADHAY CCIEMGLGMI KAIEQFCQEK KEMVNMRVGV HTGTVLCGIL | 500 |
| Human IX | GMRRFKFDVW SNDVNLANLM EQLGVAGKVH ISEATAKYLD DRYEMEDGKV | 550 |
| Mouse IX | GMRRFKFDVW SNDVNLANLM EQLGVAGKVH ISEATAKYLD DRYEMEDGRV | 550 |
| Human IX | IERLGQSVVA DQLKGLKTYL ISGQRAKESR CSCAEALLSG FEVID SDVS | 600 |
| Mouse IX | IERLGQSVVA DQLKGLKTYL ISGQRAKESH CSCAEALLSG FEVID SRES | 600 |
| Human IX | SGPRGQGTAS SG VSDLAQT VKTFDNLKTC PSCGITFAPK SEAGAEGGAP | 650 |
| Mouse IX | SGPRGQGTAS FG VSDLAQT VKTFDNLKTC PSCGITFAPK SEAGAEGGTV | 650 |
| Human IX | QNGCQDE KN STKASGGPNP KTQNGLLSPP EEKLTNSQT SLCEILQEKG | 700 |
| Mouse IX | QNGCQDE KT STKASGGPNS KTQNGLLSPP EEKLTNSQT SLCEILQEKG | 700 |
| Human IX | RWAGVSLDQS ALLPLRFKNI REKTDAHFVD VIKEDSLMKD YFFKPPINQF | 750 |
| Mouse IX | RWAGVSLDQS ALLPLRFKNI REKTDAHFVD VIKEDSLMKD YFFKPPINQF | 750 |

FIG. 3C

| | | | | |
|---|---|---|---|---|
| Human IX | SLNFLDQELE RSYRTSYQEE VIKNSPVKTF AS | TFSSLLD VFLSTTVFLI | 800 |
| Mouse IX | SLNFLDQELE RSYRTSYQEE VIKNSPVKTF AS | TFSSLLD VFLSTTVFLI | 800 |
| Human IX | LSTTCFLKYE AATVPPPPAA LAVFS | AP LLL EVLSLAVSIR MVFFLEDVMA | 850 |
| Mouse IX | LSTTCFLKYG ATATPPPPAA LAVF | GA LLL EVLSLVVSIR MVFFLEDVMT | 850 |
| Human IX | CTKLLEWIA GWLPRHCIGA ILVSLPALAV YSHMTSEMET NIHFPVFTGS | | 900 |
| Mouse IX | CTKMLLEWIA GWLPRHCIGA ILVSLPALAV YSHTTSEFET NHVTMFTGS | | 900 |
| Human IX | AMIIAVVHYC NFCQLSSSWMR SSLATVGAG FLILIVSLC DSSVLLSPL | | 950 |
| Mouse IX | AMILAVVHYC NFCQLSSSWMR SSLATIVGAG LLIIVHISLC QDSSIVMSPL | | 950 |
| Human IX | DAVQNFSSER NPCNSSVPD RRPASLICQ EVIMFFLLL LLVWFLNREF | | 1000 |
| Mouse IX | DSAQNFSAQR NPCNSSVLQD GRRPASLIGK ELILFFLLL LLVWFLNREF | | 1000 |
| Human IX | EVSYRLHYHG DVEADLHRTK IQSMRDQADW LLRNIIPYHV AEQLKVSQTY | | 1050 |
| Mouse IX | EVSYRLHYHG DVEADLHRTK IQSMRDQADW LLRNIIPYHV AEQLKVSQTY | | 1050 |
| Human IX | SKNHDSGGVI FASIVNFSEF YEENYEGGKE CYRVLNELIG DFDELLSKPD | | 1100 |
| Mouse IX | SKNHDSGGVI FASIVNFSEF YEENYEGGKE CYRVLNELIG DFDELLSKPD | | 1100 |

FIG. 3D

| | | | |
|---|---|---|---|
| Human IX | Y<span style="border:1px solid">SIEKIKTI</span> GATYMAASGL NTAQ<span style="border:1px solid">Q</span>QG<span style="border:1px solid">H</span> PQEHL<span style="border:1px solid">Q</span><span style="border:1px solid">ILFE FAKEMMRVVD</span> | 1150 |
| Mouse IX | Y<span style="border:1px solid">N</span><span style="border:1px solid">SIEKIKTI GATYMAASGL NTAQ</span>C<span style="border:1px solid">QEGH</span> PQEHL<span style="border:1px solid">R</span><span style="border:1px solid">ILFE FAKEMMRVVD</span> | 1150 |

| Human IX | DFNNMLWFN FKLRVGFNHG PLTAGVIGTT KLLYDIWGDT VNIASRMDTT | 1200 |
| Mouse IX | DFNNMLWFN FKLRVGFNHG PLTAGVIGTT KLLYDIWGDT VNIASRMDTT | 1200 |

| Human IX | GVECRIQVSE ESYRVLSKMG YDFDYRGTVN VKGKGQMKTY LYPKCTD<span style="border:1px solid">H</span><span style="border:1px solid">F</span><span style="border:1px solid">V</span> | 1250 |
| Mouse IX | GVECRIQVSE ESYRVLSKMG YDFDYRGTVN VKGKGQMKTY LYPKCTD<span style="border:1px solid">NG</span><span style="border:1px solid">M</span> | 1250 |

| Human IX | IF------ AP AVHLP---- -------- ---<span style="border:1px solid">R</span><span style="border:1px solid">H</span><span style="border:1px solid">PR</span>---- ---------- | 1265 |
| Mouse IX | V<span style="border:1px solid">FD</span>HQLSI<span style="border:1px solid">EP</span> DIRVQVDGSI G<span style="border:1px solid">RSP</span><span style="border:1px solid">T</span>DELAN LVP<span style="border:1px solid">S</span>VQYSDK ASLGSDDSTQ | 1300 |

| Human IX | ---------- ---------- G<span style="border:1px solid">M</span><span style="border:1px solid">D</span>HRTVSHR <span style="border:1px solid">R</span>--------- I<span style="border:1px solid">D</span>DPGAF-- -CPVCGQDI<span style="border:1px solid">S</span> | 1292 |
| Mouse IX | AKEARLSSKR SW<span style="border:1px solid">R</span>EPVKAEE R<span style="border:1px solid">F</span>PFGKAIEK DS<span style="border:1px solid">C</span>EDIGVEE ASELSKLNV<span style="border:1px solid">S</span> | 1350 |

| Human IX | -GF | 1294 |
| Mouse IX | KSV | 1353 |

SEQUENCE LISTING

<160> NUMBER OF SEQ ID NOS: 3

<210> SEQ ID NO 1
<211> LENGTH: 4985
<212> TYPE: DNA
<213> ORGANISM: human type IX adenylyl cyclase
<220> FEATURE:
<221> NAME/KEY: CDS
<222> LOCATION: (17)..(3898)

<400> SEQUENCE: 1

```
cccgggactc gacaac atg gct tcc ccg ccc cac cag cag ctg ctg cat cac         52
                  Met Ala Ser Pro Pro His Gln Gln Leu Leu His His
                  1               5                  10 cac agc acc gag gtg agc tgc gac tcc agc ggg gac agc aac agc gtg          100
His Ser Thr Glu Val Ser Cys Asp Ser Ser Gly Asp Ser Asn Ser Val
        15                  20                  25 cgc gtc aag atc aac ccc aag cag ctg tcc tcc aac agc cac ccc aag          148
Arg Val Lys Ile Asn Pro Lys Gln Leu Ser Ser Asn Ser His Pro Lys
 30                  35                  40 cac tgc aaa tac agc atc tcc tct agc tgc agc agc tct ggg gac tcc         196
His Cys Lys Tyr Ser Ile Ser Ser Ser Cys Ser Ser Ser Gly Asp Ser
 45                  50                  55                  60 ggg ggc gtc ccc cgg cga gtg ggc ggc gga ggc cgg ctg cgc agg cag         244
Gly Gly Val Pro Arg Arg Val Gly Gly Gly Gly Arg Leu Arg Arg Gln
                 65                  70                  75 aag aag ctg ccc cag ctg ttc gag agg gcc tcc agc cgc tgg tgg gac         292
Lys Lys Leu Pro Gln Leu Phe Glu Arg Ala Ser Ser Arg Trp Trp Asp
         80                  85                  90 ccc aag ttc gac tcg gtg aac ctg gag gag gcc tgc ctg gag cgc tgc         340
Pro Lys Phe Asp Ser Val Asn Leu Glu Glu Ala Cys Leu Glu Arg Cys
             95                 100                 105 ttc ccg cag acc cag cgc cgg ttc cgg tat gcg ctc ttc tac atc ggc         388
Phe Pro Gln Thr Gln Arg Arg Phe Arg Tyr Ala Leu Phe Tyr Ile Gly
        110                 115                 120 ttc gcc tgc ctt ctg tgg agc atc tat ttt gcg gtc cac atg aga tcc         436
Phe Ala Cys Leu Leu Trp Ser Ile Tyr Phe Ala Val His Met Arg Ser
125                 130                 135                 140 aga ctg atc gtc atg gtc gcc ccc gcg ctg tgc ttc ctc ctg gtg tgt         484
Arg Leu Ile Val Met Val Ala Pro Ala Leu Cys Phe Leu Leu Val Cys
                145                 150                 155 gtg ggc ttc ttt ctg ttt acc ttc acc aag ctg tac gcc cgg cat tac         532
Val Gly Phe Phe Leu Phe Thr Phe Thr Lys Leu Tyr Ala Arg His Tyr
            160                 165                 170 gcg tgg acc tcg ctg gct ctc acc ctg ctg gtg ttc gcc ctg acc ctg         580
Ala Trp Thr Ser Leu Ala Leu Thr Leu Leu Val Phe Ala Leu Thr Leu
        175                 180                 185 gct gcg cag ttc cag gtc ttg acg cct gtc tca gga cgc ggc gac agc         628
Ala Ala Gln Phe Gln Val Leu Thr Pro Val Ser Gly Arg Gly Asp Ser
    190                 195                 200 tcc aac ctt acg gcc aca gcc cgg ccc aca gat act tgc tta tct caa         676
Ser Asn Leu Thr Ala Thr Ala Arg Pro Thr Asp Thr Cys Leu Ser Gln
205                 210                 215                 220 gtg ggg agc ttc tcc atg tgc atc gaa gtg ctc ttt ttg ctc tat acc         724
Val Gly Ser Phe Ser Met Cys Ile Glu Val Leu Phe Leu Leu Tyr Thr
                225                 230                 235 gtc atg cac tta cct ttg tac ctg agt ttg tgt ctg ggg gtg gcc tac         772
Val Met His Leu Pro Leu Tyr Leu Ser Leu Cys Leu Gly Val Ala Tyr
            240                 245                 250
```

```
tct gtc ctt ttc gag acc ttt ggc tac cat ttc cgg gat gaa gcc tgc      820
Ser Val Leu Phe Glu Thr Phe Gly Tyr His Phe Arg Asp Glu Ala Cys
        255                 260                 265 ttc ccc tcg ccc gga gcc ggg gcc ctg cac tgg gag ctg ctg agc agg      868
Phe Pro Ser Pro Gly Ala Gly Ala Leu His Trp Glu Leu Leu Ser Arg
270                 275                 280 ggg ctg ctc cac ggc tgc atc cac gcc atc ggg gtc cac ctg ttc gtc      916
Gly Leu Leu His Gly Cys Ile His Ala Ile Gly Val His Leu Phe Val
285                 290                 295                 300 atg tcc cag gtg agg tcc agg agc acc ttc ctc aag gtg ggg caa tcc      964
Met Ser Gln Val Arg Ser Arg Ser Thr Phe Leu Lys Val Gly Gln Ser
                305                 310                 315 att atg cac ggg aag gac ctg gaa gtg gaa aaa gcc ctc aaa gag agg     1012
Ile Met His Gly Lys Asp Leu Glu Val Glu Lys Ala Leu Lys Glu Arg
        320                 325                 330 atg att cat tcc gtg atg cca aga atc ata gcc gat gac tta atg aag     1060
Met Ile His Ser Val Met Pro Arg Ile Ile Ala Asp Asp Leu Met Lys
                335                 340                 345 cag gga gat gag gag agt gag aat tct gtc aag agg cat gcc acc tcg     1108
Gln Gly Asp Glu Glu Ser Glu Asn Ser Val Lys Arg His Ala Thr Ser
350                 355                 360 agc ccc aag aac agg aag aaa aag tct tcc atc caa aaa gct cct ata     1156
Ser Pro Lys Asn Arg Lys Lys Lys Ser Ser Ile Gln Lys Ala Pro Ile
365                 370                 375                 380 gcc ttc cgc cct ttt aag atg cag cag atc gaa gaa gtc agt att tta     1204
Ala Phe Arg Pro Phe Lys Met Gln Gln Ile Glu Glu Val Ser Ile Leu
                385                 390                 395 ttt gca gat atc gtg ggc ttc acc aag atg agt gcc aac aag tct gcc     1252
Phe Ala Asp Ile Val Gly Phe Thr Lys Met Ser Ala Asn Lys Ser Ala
                400                 405                 410 cac gcc ctg gtg ggt ctc ctg aac gat ctg ttc ggt cgc ttc gac cgc     1300
His Ala Leu Val Gly Leu Leu Asn Asp Leu Phe Gly Arg Phe Asp Arg
        415                 420                 425 ctg tgt gag gag acc aag tgt gag aaa atc agc acc ctg gga gac tgt     1348
Leu Cys Glu Glu Thr Lys Cys Glu Lys Ile Ser Thr Leu Gly Asp Cys
        430                 435                 440 tac tac tgc gtg gcg ggc tgt ccc gag ccc cgg gcc gac cat gcc tac     1396
Tyr Tyr Cys Val Ala Gly Cys Pro Glu Pro Arg Ala Asp His Ala Tyr
445                 450                 455                 460 tgc tgc atc gag atg ggc ctg ggc atg atc aag gcc atc gag cag ttc     1444
Cys Cys Ile Glu Met Gly Leu Gly Met Ile Lys Ala Ile Glu Gln Phe
                465                 470                 475 tgc cag gag aag aag gag atg gtg aac atg aga gtc ggg gtg cac acg     1492
Cys Gln Glu Lys Lys Glu Met Val Asn Met Arg Val Gly Val His Thr
                480                 485                 490 ggc acc gtc ctt tgc ggc atc ctg ggc atg agg agg ttt aaa ttt gac     1540
Gly Thr Val Leu Cys Gly Ile Leu Gly Met Arg Arg Phe Lys Phe Asp
        495                 500                 505 gtg tgg tcc aac gat gtg aac ctg gcc aat ctc atg gag cag ctg gga     1588
Val Trp Ser Asn Asp Val Asn Leu Ala Asn Leu Met Glu Gln Leu Gly
510                 515                 520 gtg gcc ggc aaa gtt cac att tct gag gcc acc gca aaa tac tta gat     1636
Val Ala Gly Lys Val His Ile Ser Glu Ala Thr Ala Lys Tyr Leu Asp
525                 530                 535                 540 gac cgg tac gaa atg gaa gat ggg aaa gtt att gaa cgg ctg ggc cag     1684
Asp Arg Tyr Glu Met Glu Asp Gly Lys Val Ile Glu Arg Leu Gly Gln
                545                 550                 555 agc gtg gtt gct gac cag ttg aaa ggt ttg aag aca tac ctg ata tcg     1732
Ser Val Val Ala Asp Gln Leu Lys Gly Leu Lys Thr Tyr Leu Ile Ser
        560                 565                 570
```

-continued

```
ggt cag aga gcc aag gag tct cgc tgc agc tgt gca gag gcc ttg ctt        1780
Gly Gln Arg Ala Lys Glu Ser Arg Cys Ser Cys Ala Glu Ala Leu Leu
        575                 580                 585 tct ggc ttt gag gtc att gac ggc tca cag gtg tcc tca ggc cct agg        1828
Ser Gly Phe Glu Val Ile Asp Gly Ser Gln Val Ser Ser Gly Pro Arg
    590                 595                 600 gga cag ggg aca gcg tca tca ggg aat gtc agt gac ttg gcg cag act        1876
Gly Gln Gly Thr Ala Ser Ser Gly Asn Val Ser Asp Leu Ala Gln Thr
605                 610                 615                 620 gtc aaa acc ttt gat aac ctt aag acc tgc cct tcg tgc gga atc aca        1924
Val Lys Thr Phe Asp Asn Leu Lys Thr Cys Pro Ser Cys Gly Ile Thr
                625                 630                 635 ttt gct ccc aaa tct gaa gcc ggc gcc gag gga gga gca cct caa aac        1972
Phe Ala Pro Lys Ser Glu Ala Gly Ala Glu Gly Gly Ala Pro Gln Asn
            640                 645                 650 ggc tgc caa gac gag cat aaa aac agc acc aag gct tct gga gga cct        2020
Gly Cys Gln Asp Glu His Lys Asn Ser Thr Lys Ala Ser Gly Gly Pro
        655                 660                 665 aat ccc aaa act cag aac ggg ctc ctc agc cct ccc caa gag gag aag        2068
Asn Pro Lys Thr Gln Asn Gly Leu Leu Ser Pro Pro Gln Glu Glu Lys
670                 675                 680 ctc acc aac agt cag act tct ctg tgt gag atc ttg cag gag aag gga        2116
Leu Thr Asn Ser Gln Thr Ser Leu Cys Glu Ile Leu Gln Glu Lys Gly
685                 690                 695                 700 agg tgg gca ggg gtg agc ctg gac cag tcg gct ctc ctt ccg ctg agg        2164
Arg Trp Ala Gly Val Ser Leu Asp Gln Ser Ala Leu Leu Pro Leu Arg
                705                 710                 715 ttc aag aac atc cgg gag aaa acg gac gcc cac ttt gtg gac gtt atc        2212
Phe Lys Asn Ile Arg Glu Lys Thr Asp Ala His Phe Val Asp Val Ile
            720                 725                 730 aaa gaa gac agc ctg atg aaa gat tac ttt ttt aag ccg ccc att aat        2260
Lys Glu Asp Ser Leu Met Lys Asp Tyr Phe Phe Lys Pro Pro Ile Asn
        735                 740                 745 cag ttc agc ctg aac ttc ctg gat cag gag ctg gag cga tcc tac agg        2308
Gln Phe Ser Leu Asn Phe Leu Asp Gln Glu Leu Glu Arg Ser Tyr Arg
    750                 755                 760 acc agc tat cag gaa gag gtc ata aag aac tcc ccc gtg aag acg ttt        2356
Thr Ser Tyr Gln Glu Glu Val Ile Lys Asn Ser Pro Val Lys Thr Phe
765                 770                 775                 780 gct agt ccc acc ttc agc tcc ctc ctg gat gtg ttt ctg tcg acc aca        2404
Ala Ser Pro Thr Phe Ser Ser Leu Leu Asp Val Phe Leu Ser Thr Thr
                785                 790                 795 gtg ttt ctg acg ctg tcc acc acc tgc ttc ctg aag tac gag gcg gcc        2452
Val Phe Leu Thr Leu Ser Thr Thr Cys Phe Leu Lys Tyr Glu Ala Ala
            800                 805                 810 acc gtg cct ccc ccg ccc gcc gcc ctg gcg gtc ttc agt gca gcc ctg        2500
Thr Val Pro Pro Pro Pro Ala Ala Leu Ala Val Phe Ser Ala Ala Leu
        815                 820                 825 ctg ctg gag gtg ctg tcc ctc gcg gtg tcc atc agg atg gtg ttc ttc        2548
Leu Leu Glu Val Leu Ser Leu Ala Val Ser Ile Arg Met Val Phe Phe
    830                 835                 840 ctg gag gac gtc atg gcc tgc acc aag cgc ctg ctg gag tgg atc gcc        2596
Leu Glu Asp Val Met Ala Cys Thr Lys Arg Leu Leu Glu Trp Ile Ala
845                 850                 855                 860 ggc tgg cta cca cgt cac tgc atc ggg gca atc ctg gtg tcg ctt ccc        2644
Gly Trp Leu Pro Arg His Cys Ile Gly Ala Ile Leu Val Ser Leu Pro
                865                 870                 875 gca ctg gcc gtc tac tcc cat gtc acc tcc gaa tat gag acc aac ata        2692
Ala Leu Ala Val Tyr Ser His Val Thr Ser Glu Tyr Glu Thr Asn Ile
```

-continued

|  |  |  |  |  |  |  |
|---|---|---|---|---|---|---|
| 880 | | 885 | | 890 | | |

```
cac ttc cca gtg ttc aca ggc tcg gcc gca ctg att gcc gtc gtg cac      2740
His Phe Pro Val Phe Thr Gly Ser Ala Ala Leu Ile Ala Val Val His
        895                 900                 905 tac tgt aac ttc tgc cag ctc agc tcc tgg atg agg tcc tcc ctc gcc      2788
Tyr Cys Asn Phe Cys Gln Leu Ser Ser Trp Met Arg Ser Ser Leu Ala
910                 915                 920 acc gtc gtg ggg gcc ggg ccg ctg ctg ctc tac gtc tcc ctg tgc          2836
Thr Val Val Gly Ala Gly Pro Leu Leu Leu Leu Tyr Val Ser Leu Cys
925                 930                 935                 940 cca gac agt tct gta tta act tcg ccc ctt gac gca gta cag aat ttc      2884
Pro Asp Ser Ser Val Leu Thr Ser Pro Leu Asp Ala Val Gln Asn Phe
            945                 950                 955 agt tcc gag agg aac ccg tgc aat agt tcg gtg ccg cgt gac ctc cgg      2932
Ser Ser Glu Arg Asn Pro Cys Asn Ser Ser Val Pro Arg Asp Leu Arg
        960                 965                 970 cgg ccc gcc agc ctc atc ggc cag gag gtg gtt ctc gtc ttc ttt ctc      2980
Arg Pro Ala Ser Leu Ile Gly Gln Glu Val Val Leu Val Phe Phe Leu
    975                 980                 985 ctg ctc ttg ttg gtc tgg ttc ctg aat cgc gaa ttt gaa gtc agc tac      3028
Leu Leu Leu Leu Val Trp Phe Leu Asn Arg Glu Phe Glu Val Ser Tyr
990                 995                 1000 cgc ctc cac tac cac gga gac gtg gaa gcg gat ctt cac cgc acc aag      3076
Arg Leu His Tyr His Gly Asp Val Glu Ala Asp Leu His Arg Thr Lys
1005                1010                1015                1020 atc cag agc atg cgg gac cag gca gac tgg ctg ctg agg aac atc atc      3124
Ile Gln Ser Met Arg Asp Gln Ala Asp Trp Leu Leu Arg Asn Ile Ile
                1025                1030                1035 ccc tac cac gtg gct gag cag ctg aag gtg tcc cag acc tac tcc aag      3172
Pro Tyr His Val Ala Glu Gln Leu Lys Val Ser Gln Thr Tyr Ser Lys
            1040                1045                1050 aac cac gac agc gga ggg gtg atc ttc gcc agc atc gtc aac ttc agc      3220
Asn His Asp Ser Gly Gly Val Ile Phe Ala Ser Ile Val Asn Phe Ser
        1055                1060                1065 gag ttc tac gag gag aac tac gag ggc ggc aag gag tgc tac cgg gtc      3268
Glu Phe Tyr Glu Glu Asn Tyr Glu Gly Gly Lys Glu Cys Tyr Arg Val
    1070                1075                1080 ctc aac gag ctc atc ggg gac ttt gac gag ctc cta agc aag ccg gac      3316
Leu Asn Glu Leu Ile Gly Asp Phe Asp Glu Leu Leu Ser Lys Pro Asp
1085                1090                1095                1100 tac agc agc atc gag aag atc aag acc atc gga gcc acg tac atg gcg      3364
Tyr Ser Ser Ile Glu Lys Ile Lys Thr Ile Gly Ala Thr Tyr Met Ala
                1105                1110                1115 gcg tca ggg ctg aac acc gcg cag gcc cag gac ggc agc cac ccg cag      3412
Ala Ser Gly Leu Asn Thr Ala Gln Ala Gln Asp Gly Ser His Pro Gln
            1120                1125                1130 gag cac ctg cag atc ctg ttc gag ttc gcc aag gag atg atg cgc gtg      3460
Glu His Leu Gln Ile Leu Phe Glu Phe Ala Lys Glu Met Met Arg Val
        1135                1140                1145 gtg gac gac ttc aac aac aac atg ctg tgg ttc aac ttc aag ctc cgc      3508
Val Asp Asp Phe Asn Asn Asn Met Leu Trp Phe Asn Phe Lys Leu Arg
    1150                1155                1160 gtc ggc ttc aac cat ggg ccc ctc acg gcc ggg gtc atc ggc acc acc      3556
Val Gly Phe Asn His Gly Pro Leu Thr Ala Gly Val Ile Gly Thr Thr
1165                1170                1175                1180 aag ctg ctg tac gac atc tgg gga gac acc gtc aac atc gcc agc agg      3604
Lys Leu Leu Tyr Asp Ile Trp Gly Asp Thr Val Asn Ile Ala Ser Arg
                1185                1190                1195 atg gac acc acc ggc gtg gag tgc cgc atc cag gtg agc gaa gag agc      3652
```

-continued

| | | | | | | | | | | | | |
|---|---|---|---|---|---|---|---|---|---|---|---|---|
|Met|Asp|Thr|Thr|Gly|Val|Glu|Cys|Arg|Ile|Gln|Val|Ser|Glu|Glu|Ser|
| | | |1200| | |1205| | | |1210| | | | | |

```
tac cgc gtc ttg agc aag atg ggc tat gac ttc gac tac aga ggg acc      3700
Tyr Arg Val Leu Ser Lys Met Gly Tyr Asp Phe Asp Tyr Arg Gly Thr
        1215                1220                1225 gtg aat gtc aag ggg aaa ggc cag atg aag acc tac ctg tac cca aag      3748
Val Asn Val Lys Gly Lys Gly Gln Met Lys Thr Tyr Leu Tyr Pro Lys
    1230                1235                1240 tgc acg gat cac agg gtc atc cca gca cca gct gtc cat ctc ccc aga      3796
Cys Thr Asp His Arg Val Ile Pro Ala Pro Ala Val His Leu Pro Arg
1245                1250                1255                1260 cat ccg cgt cca ggt gga tgg cag cat cgg acg gtc tcc cac aga cga      3844
His Pro Arg Pro Gly Gly Trp Gln His Arg Thr Val Ser His Arg Arg
                1265                1270                1275 gat tgc caa cct ggt gcc ttc tgt cca gta tgt gga caa gac atc tct      3892
Asp Cys Gln Pro Gly Ala Phe Cys Pro Val Cys Gly Gln Asp Ile Ser
            1280                1285                1290 ggg ttc tgacagcagc acgcaggcca aggatgccca cctgtccccc aagagaccgt       3948
Gly Phe ggaaggagcc cgtcaaagcc gaagaaaggg gtcgatttgg caaagccata gagaaagacg    4008
actgtgacga acaggaata gaagaagcca acgaactcac caagctcaac gtttcaaaga     4068
gtgtgtgagg cggcgcccac ccgctgcccg aggtgctctg tttgtcgaaa cacagtaata    4128
tttgtatttg gctgttgtgc tttccaagcg ccacagttgc cctccccgga cgtggtgtta    4188
tgtggtcatt tcagccctaa cttctgtgtg gatcacagtt attcagggtt cattttcatc    4248
cattcttccc tttcgctccc ttccctggaa accccgctgc ctctgggtca tccgttcagc    4308
acgtggtgga gaacaagtgc cttcagggct ggcctcggcc tcgagtctcg ggacagaggc    4368
cgccagtgga gatcatggct ttgggtatta tttgactttt agaacaaaag ctgtggttaa    4428
gatctcattt ttattgcttt ttcccacgtc ccacgagaca ctattttcgg ttctctggct    4488 aatacctgt ttttgagttt attttgtttc tgtctatgtc acagtgtccc cctacgaccc     4548
gacctctcta tgtaagcaca catgcgcaca cacacttgca ttcatgaatc tgatataaag    4608
tgccagtaat ccgccaagag gggtgcgaa ggggggcatgt cacgacagct ccgccacccc    4668
ccattgccca cccgcacttt cccgagcacc gcgccccgtg ggctgtgggt gagccgcgct    4728
ccctgcactg agcgggttta ggggctcgcc cacatgcatg caggccaaga cagcaaatgc    4788
cagccgggca cgacgcctgt gtgcccaggc ctcgggggtc tcagagccgc ctctcacccc    4848
cgaccctcca cccaggggtc tccccgtcgg gagtggaggc gttggtcctg gaagctgact    4908
catcggagag ggaaatacca aataaacatc cgaggttgca aaaaaaaaa aaaaaaaaa      4968 aaaaaaaaa aaaaaaa                                                    4985
```

<210> SEQ ID NO 2
<211> LENGTH: 1294
<212> TYPE: PRT
<213> ORGANISM: human type IX adenylyl cyclase

<400> SEQUENCE: 2

| | | | | | | | | | | | | | | | |
|---|---|---|---|---|---|---|---|---|---|---|---|---|---|---|---|
|Met|Ala|Ser|Pro|Pro|His|Gln|Gln|Leu|Leu|His|His|His|Ser|Thr|Glu|
|1| | | |5| | | | |10| | | | |15| |

| | | | | | | | | | | | | | | | |
|---|---|---|---|---|---|---|---|---|---|---|---|---|---|---|---|
|Val|Ser|Cys|Asp|Ser|Ser|Gly|Asp|Ser|Asn|Ser|Val|Arg|Val|Lys|Ile|
| | | | |20| | | | |25| | | | |30| |

| | | | | | | | | | | | | | |
|---|---|---|---|---|---|---|---|---|---|---|---|---|---|
|Asn|Pro|Lys|Gln|Leu|Ser|Ser|Asn|Ser|His|Pro|Lys|His|Cys|Lys|Tyr|
| | | | |35| | | | |40| | | | |45| |

| | | | | | | | | | | | | | | | |
|---|---|---|---|---|---|---|---|---|---|---|---|---|---|---|---|
|Ser|Ile|Ser|Ser|Ser|Cys|Ser|Ser|Ser|Gly|Asp|Ser|Gly|Gly|Val|Pro|

-continued

```
                50                   55                   60
Arg Arg Val Gly Gly Gly Arg Leu Arg Gln Lys Lys Leu Pro
 65                   70                   75                   80

Gln Leu Phe Glu Arg Ala Ser Ser Arg Trp Trp Asp Pro Lys Phe Asp
                 85                   90                   95

Ser Val Asn Leu Glu Glu Ala Cys Leu Glu Arg Cys Phe Pro Gln Thr
                100                  105                  110

Gln Arg Arg Phe Arg Tyr Ala Leu Phe Tyr Ile Gly Phe Ala Cys Leu
                115                  120                  125

Leu Trp Ser Ile Tyr Phe Ala Val His Met Arg Ser Arg Leu Ile Val
130                  135                  140

Met Val Ala Pro Ala Leu Cys Phe Leu Leu Val Cys Val Gly Phe Phe
145                  150                  155                  160

Leu Phe Thr Phe Thr Lys Leu Tyr Ala Arg His Tyr Ala Trp Thr Ser
                165                  170                  175

Leu Ala Leu Thr Leu Leu Val Phe Ala Leu Thr Leu Ala Ala Gln Phe
                180                  185                  190

Gln Val Leu Thr Pro Val Ser Gly Arg Gly Asp Ser Ser Asn Leu Thr
                195                  200                  205

Ala Thr Ala Arg Pro Thr Asp Thr Cys Leu Ser Gln Val Gly Ser Phe
210                  215                  220

Ser Met Cys Ile Glu Val Leu Phe Leu Leu Tyr Thr Val Met His Leu
225                  230                  235                  240

Pro Leu Tyr Leu Ser Leu Cys Leu Gly Val Ala Tyr Ser Val Leu Phe
                245                  250                  255

Glu Thr Phe Gly Tyr His Phe Arg Asp Glu Ala Cys Phe Pro Ser Pro
                260                  265                  270

Gly Ala Gly Ala Leu His Trp Glu Leu Leu Ser Arg Gly Leu Leu His
                275                  280                  285

Gly Cys Ile His Ala Ile Gly Val His Leu Phe Val Met Ser Gln Val
290                  295                  300

Arg Ser Arg Ser Thr Phe Leu Lys Val Gly Gln Ser Ile Met His Gly
305                  310                  315                  320

Lys Asp Leu Glu Val Glu Lys Ala Leu Lys Glu Arg Met Ile His Ser
                325                  330                  335

Val Met Pro Arg Ile Ile Ala Asp Asp Leu Met Lys Gln Gly Asp Glu
                340                  345                  350

Glu Ser Glu Asn Ser Val Lys Arg His Ala Thr Ser Ser Pro Lys Asn
                355                  360                  365

Arg Lys Lys Lys Ser Ser Ile Gln Lys Ala Pro Ile Ala Phe Arg Pro
370                  375                  380

Phe Lys Met Gln Gln Ile Glu Glu Val Ser Ile Leu Phe Ala Asp Ile
385                  390                  395                  400

Val Gly Phe Thr Lys Met Ser Ala Asn Lys Ser Ala His Ala Leu Val
                405                  410                  415

Gly Leu Leu Asn Asp Leu Phe Gly Arg Phe Asp Arg Leu Cys Glu Glu
                420                  425                  430

Thr Lys Cys Glu Lys Ile Ser Thr Leu Gly Asp Cys Tyr Tyr Cys Val
                435                  440                  445

Ala Gly Cys Pro Glu Pro Arg Ala Asp His Ala Tyr Cys Cys Ile Glu
                450                  455                  460

Met Gly Leu Gly Met Ile Lys Ala Ile Glu Gln Phe Cys Gln Glu Lys
465                  470                  475                  480
```

```
Lys Glu Met Val Asn Met Arg Val Gly Val His Thr Gly Thr Val Leu
                485                 490                 495
Cys Gly Ile Leu Gly Met Arg Arg Phe Lys Phe Asp Val Trp Ser Asn
            500                 505                 510
Asp Val Asn Leu Ala Asn Leu Met Glu Gln Leu Gly Val Ala Gly Lys
        515                 520                 525
Val His Ile Ser Glu Ala Thr Ala Lys Tyr Leu Asp Asp Arg Tyr Glu
    530                 535                 540
Met Glu Asp Gly Lys Val Ile Glu Arg Leu Gly Gln Ser Val Val Ala
545                 550                 555                 560
Asp Gln Leu Lys Gly Leu Lys Thr Tyr Leu Ile Ser Gly Gln Arg Ala
                565                 570                 575
Lys Glu Ser Arg Cys Ser Cys Ala Glu Ala Leu Leu Ser Gly Phe Glu
            580                 585                 590
Val Ile Asp Gly Ser Gln Val Ser Ser Gly Pro Arg Gly Gln Gly Thr
        595                 600                 605
Ala Ser Ser Gly Asn Val Ser Asp Leu Ala Gln Thr Val Lys Thr Phe
    610                 615                 620
Asp Asn Leu Lys Thr Cys Pro Ser Cys Gly Ile Thr Phe Ala Pro Lys
625                 630                 635                 640
Ser Glu Ala Gly Ala Glu Gly Gly Ala Pro Gln Asn Gly Cys Gln Asp
                645                 650                 655
Glu His Lys Asn Ser Thr Lys Ala Ser Gly Gly Pro Asn Pro Lys Thr
            660                 665                 670
Gln Asn Gly Leu Leu Ser Pro Gln Glu Glu Lys Leu Thr Asn Ser
        675                 680                 685
Gln Thr Ser Leu Cys Glu Ile Leu Gln Glu Lys Gly Arg Trp Ala Gly
    690                 695                 700
Val Ser Leu Asp Gln Ser Ala Leu Leu Pro Leu Arg Phe Lys Asn Ile
705                 710                 715                 720
Arg Glu Lys Thr Asp Ala His Phe Val Asp Val Ile Lys Glu Asp Ser
                725                 730                 735
Leu Met Lys Asp Tyr Phe Phe Lys Pro Pro Ile Asn Gln Phe Ser Leu
            740                 745                 750
Asn Phe Leu Asp Gln Glu Leu Glu Arg Ser Tyr Arg Thr Ser Tyr Gln
        755                 760                 765
Glu Glu Val Ile Lys Asn Ser Pro Val Lys Thr Phe Ala Ser Pro Thr
    770                 775                 780
Phe Ser Ser Leu Leu Asp Val Phe Leu Ser Thr Thr Val Phe Leu Thr
785                 790                 795                 800
Leu Ser Thr Thr Cys Phe Leu Lys Tyr Glu Ala Ala Thr Val Pro Pro
                805                 810                 815
Pro Pro Ala Ala Leu Ala Val Phe Ser Ala Ala Leu Leu Leu Glu Val
            820                 825                 830
Leu Ser Leu Ala Val Ser Ile Arg Met Val Phe Phe Leu Glu Asp Val
        835                 840                 845
Met Ala Cys Thr Lys Arg Leu Leu Glu Trp Ile Ala Gly Trp Leu Pro
850                 855                 860
Arg His Cys Ile Gly Ala Ile Leu Val Ser Leu Pro Ala Leu Ala Val
865                 870                 875                 880
Tyr Ser His Val Thr Ser Glu Tyr Glu Thr Asn Ile His Phe Pro Val
                885                 890                 895
```

```
Phe Thr Gly Ser Ala Ala Leu Ile Ala Val Val His Tyr Cys Asn Phe
            900                 905                 910

Cys Gln Leu Ser Ser Trp Met Arg Ser Ser Leu Ala Thr Val Val Gly
        915                 920                 925

Ala Gly Pro Leu Leu Leu Tyr Val Ser Leu Cys Pro Asp Ser Ser
    930                 935                 940

Val Leu Thr Ser Pro Leu Asp Ala Val Gln Asn Phe Ser Ser Glu Arg
945                 950                 955                 960

Asn Pro Cys Asn Ser Ser Val Pro Arg Asp Leu Arg Arg Pro Ala Ser
                965                 970                 975

Leu Ile Gly Gln Glu Val Val Leu Val Phe Phe Leu Leu Leu Leu Leu
            980                 985                 990

Val Trp Phe Leu Asn Arg Glu Phe Glu Val Ser Tyr Arg Leu His Tyr
            995                 1000                1005

His Gly Asp Val Glu Ala Asp Leu His Arg Thr Lys Ile Gln Ser Met
    1010                1015                1020

Arg Asp Gln Ala Asp Trp Leu Leu Arg Asn Ile Ile Pro Tyr His Val
1025                1030                1035                1040

Ala Glu Gln Leu Lys Val Ser Gln Thr Tyr Ser Lys Asn His Asp Ser
            1045                1050                1055

Gly Gly Val Ile Phe Ala Ser Ile Val Asn Phe Ser Glu Phe Tyr Glu
            1060                1065                1070

Glu Asn Tyr Glu Gly Gly Lys Glu Cys Tyr Arg Val Leu Asn Glu Leu
        1075                1080                1085

Ile Gly Asp Phe Asp Glu Leu Leu Ser Lys Pro Asp Tyr Ser Ser Ile
    1090                1095                1100

Glu Lys Ile Lys Thr Ile Gly Ala Thr Tyr Met Ala Ala Ser Gly Leu
1105                1110                1115                1120

Asn Thr Ala Gln Ala Gln Asp Gly Ser His Pro Gln Glu His Leu Gln
            1125                1130                1135

Ile Leu Phe Glu Phe Ala Lys Glu Met Met Arg Val Val Asp Asp Phe
        1140                1145                1150

Asn Asn Asn Met Leu Trp Phe Asn Phe Lys Leu Arg Val Gly Phe Asn
        1155                1160                1165

His Gly Pro Leu Thr Ala Gly Val Ile Gly Thr Thr Lys Leu Leu Tyr
    1170                1175                1180

Asp Ile Trp Gly Asp Thr Val Asn Ile Ala Ser Arg Met Asp Thr Thr
1185                1190                1195                1200

Gly Val Glu Cys Arg Ile Gln Val Ser Glu Glu Ser Tyr Arg Val Leu
            1205                1210                1215

Ser Lys Met Gly Tyr Asp Phe Asp Tyr Arg Gly Thr Val Asn Val Lys
        1220                1225                1230

Gly Lys Gly Gln Met Lys Thr Tyr Leu Tyr Pro Lys Cys Thr Asp His
    1235                1240                1245

Arg Val Ile Pro Ala Pro Ala Val His Leu Pro Arg His Pro Arg Pro
1250                1255                1260

Gly Gly Trp Gln His Arg Thr Val Ser His Arg Arg Asp Cys Gln Pro
1265                1270                1275                1280

Gly Ala Phe Cys Pro Val Cys Gly Gln Asp Ile Ser Gly Phe
            1285                1290

<210> SEQ ID NO 3
<211> LENGTH: 1353
<212> TYPE: PRT
```

<213> ORGANISM: murine type IX adenylyl cyclase

<400> SEQUENCE: 3

```
Met Ala Ser Ser Pro His Gln Leu Leu His His Ser Thr Glu
 1               5                  10                  15

Val Ser Cys Asp Ser Ser Gly Asp Ser Asn Ser Val Arg Val Lys Ile
             20                  25                  30

Asn Pro Lys Gln Leu Ser Asn Ile His Pro Lys His Cys Lys Tyr
         35                  40                  45

Ser Ile Ser Ser Ser Cys Ser Ser Gly Asp Ser Gly Gly Leu Pro
     50                  55                      60

Arg Arg Val Gly Gly Gly Arg Leu Arg Gln Lys Lys Leu Pro
 65              70                  75                  80

Gln Leu Phe Glu Arg Ala Ser Ser Arg Trp Trp Asp Pro Lys Phe Asp
                 85                  90                  95

Ser Met Asn Leu Glu Glu Ala Cys Leu Glu Arg Cys Phe Pro Gln Thr
                100                 105                 110

Gln Arg Arg Phe Arg Tyr Ala Leu Phe Tyr Val Gly Phe Ala Cys Leu
                115                 120                 125

Leu Trp Ser Ile Tyr Phe Ala Val His Met Lys Ser Lys Val Ile Val
            130                 135                 140

Met Val Pro Ala Leu Cys Phe Leu Val Val Cys Val Gly Phe Phe
145                 150                 155                 160

Leu Phe Thr Phe Thr Lys Leu Tyr Ala Arg His Tyr Ala Trp Thr Ser
                165                 170                 175

Leu Ala Leu Thr Leu Leu Val Phe Ala Leu Thr Leu Ala Ala Gln Phe
                180                 185                 190

Gln Val Trp Thr Pro Leu Ser Gly Arg Val Asp Ser Ser Asn His Thr
            195                 200                 205

Leu Thr Ala Ile Pro Ala Asp Thr Cys Leu Ser Gln Val Gly Ser Phe
        210                 215                 220

Ser Ile Cys Ile Glu Val Leu Leu Leu Tyr Thr Val Met Gln Leu
225                 230                 235                 240

Pro Leu Tyr Leu Ser Leu Phe Leu Gly Val Val Tyr Ser Val Leu Phe
                245                 250                 255

Glu Thr Phe Gly Tyr His Phe Arg Asn Glu Asp Cys Tyr Pro Ser Pro
                260                 265                 270

Gly Pro Gly Ala Leu His Trp Glu Leu Leu Ser Arg Ala Leu Leu His
            275                 280                 285

Val Cys Ile His Ala Ile Gly Ile His Leu Phe Val Met Ser Gln Val
        290                 295                 300

Arg Ser Arg Ser Thr Phe Leu Lys Val Gly Gln Ser Ile Met His Gly
305                 310                 315                 320

Lys Asp Leu Glu Val Glu Lys Ala Leu Lys Glu Arg Met Ile His Ser
                325                 330                 335

Val Met Pro Arg Ile Ile Ala Asp Asp Leu Met Lys Gln Gly Asp Glu
                340                 345                 350

Glu Ser Glu Asn Ser Val Lys Arg His Ala Thr Ser Ser Pro Lys Asn
            355                 360                 365

Arg Lys Lys Lys Ser Ser Ile Gln Lys Ala Pro Ile Ala Phe Arg Pro
        370                 375                 380

Phe Lys Met Gln Gln Ile Glu Glu Val Ser Ile Leu Phe Ala Asp Ile
385                 390                 395                 400
```

-continued

```
Val Gly Phe Thr Lys Met Ser Ala Asn Lys Ser Ala His Ala Leu Val
            405                 410                 415
Gly Leu Leu Asn Asp Leu Phe Gly Arg Phe Asp Arg Leu Cys Glu Gln
                420                 425                 430
Thr Lys Cys Glu Lys Ile Ser Thr Leu Gly Asp Cys Tyr Tyr Cys Val
            435                 440                 445
Ala Gly Cys Pro Glu Pro Arg Ala Asp His Ala Tyr Cys Cys Ile Glu
450                 455                 460
Met Gly Leu Gly Met Ile Lys Ala Ile Glu Gln Phe Cys Gln Glu Lys
465                 470                 475                 480
Lys Glu Met Val Asn Met Arg Val Gly Val His Thr Gly Thr Val Leu
                485                 490                 495
Cys Gly Ile Leu Gly Met Arg Arg Phe Lys Phe Asp Val Trp Ser Asn
            500                 505                 510
Asp Val Asn Leu Ala Asn Leu Met Glu Gln Leu Gly Val Ala Gly Lys
            515                 520                 525
Val His Ile Ser Glu Ala Thr Ala Lys Tyr Leu Asp Asp Arg Tyr Glu
    530                 535                 540
Met Glu Asp Gly Arg Val Ile Glu Arg Leu Gly Gln Ser Val Val Ala
545                 550                 555                 560
Asp Gln Leu Lys Gly Leu Lys Thr Tyr Leu Ile Ser Gly Gln Arg Ala
                565                 570                 575
Lys Glu Ser His Cys Ser Cys Ala Glu Ala Leu Leu Ser Gly Phe Glu
            580                 585                 590
Val Ile Asp Asp Ser Arg Glu Ser Gly Pro Arg Gly Gln Gly Thr
    595                 600                 605
Ala Ser Pro Gly Ser Val Ser Asp Leu Ala Gln Thr Val Lys Thr Phe
    610                 615                 620
Asp Asn Leu Lys Thr Cys Pro Ser Cys Gly Ile Thr Phe Ala Pro Lys
625                 630                 635                 640
Ser Glu Ala Gly Ala Glu Gly Gly Thr Val Gln Asn Gly Cys Gln Asp
                645                 650                 655
Glu Pro Lys Thr Ser Thr Lys Ala Ser Gly Gly Pro Asn Ser Lys Thr
            660                 665                 670
Gln Asn Gly Leu Leu Ser Pro Ala Glu Glu Lys Leu Thr Asn Ser
    675                 680                 685
Gln Thr Ser Leu Cys Glu Ile Leu Gln Glu Lys Gly Arg Trp Ala Gly
    690                 695                 700
Val Ser Leu Asp Gln Ser Ala Leu Leu Pro Leu Arg Phe Lys Asn Ile
705                 710                 715                 720
Arg Glu Lys Thr Asp Ala His Phe Val Asp Val Ile Lys Glu Asp Ser
                725                 730                 735
Leu Met Lys Asp Tyr Phe Phe Lys Pro Pro Ile Asn Gln Phe Ser Leu
                740                 745                 750
Asn Phe Leu Asp Gln Glu Leu Glu Arg Ser Tyr Arg Thr Ser Tyr Gln
            755                 760                 765
Glu Glu Val Ile Lys Asn Ser Pro Val Lys Thr Phe Ala Ser Ala Thr
    770                 775                 780
Phe Ser Ser Leu Leu Asp Val Phe Leu Ser Thr Thr Val Phe Leu Ile
785                 790                 795                 800
Leu Ser Ile Thr Cys Phe Leu Lys Tyr Gly Ala Thr Ala Thr Pro Pro
                805                 810                 815
Pro Pro Ala Ala Leu Ala Val Phe Gly Ala Asp Leu Leu Leu Glu Val
```

-continued

```
                820                 825                 830
Leu Ser Leu Ile Val Ser Ile Arg Met Val Phe Phe Leu Glu Asp Val
        835                 840                 845
Met Thr Cys Thr Lys Trp Leu Leu Glu Trp Ile Ala Gly Trp Leu Pro
    850                 855                 860
Arg His Cys Ile Gly Ala Ile Leu Val Ser Leu Pro Ala Leu Ala Val
865                 870                 875                 880
Tyr Ser His Ile Thr Ser Glu Phe Glu Thr Asn Ile His Val Thr Met
                885                 890                 895
Phe Thr Gly Ser Ala Val Leu Val Ala Val Val His Tyr Cys Asn Phe
        900                 905                 910
Cys Gln Leu Ser Ser Trp Met Arg Ser Ser Leu Ala Thr Ile Val Gly
        915                 920                 925
Ala Gly Leu Leu Leu Leu His Ile Ser Leu Cys Gln Asp Ser Ser
        930                 935                 940
Ile Val Met Ser Pro Leu Asp Ser Ala Gln Asn Phe Ser Ala Gln Arg
945                 950                 955                 960
Asn Pro Cys Asn Ser Ser Val Leu Gln Asp Gly Arg Arg Pro Ala Ser
                965                 970                 975
Leu Ile Gly Lys Glu Leu Ile Leu Ile Phe Phe Leu Leu Leu Leu
        980                 985                 990
Val Trp Phe Leu Asn Arg Glu Phe Glu Val Ser Tyr Arg Leu His Tyr
        995                 1000                1005
His Gly Asp Val Glu Ala Asp Leu His Arg Thr Lys Ile Gln Ser Met
        1010                1015                1020
Arg Asp Gln Ala Asp Trp Leu Leu Arg Asn Ile Ile Pro Tyr His Val
1025                1030                1035                1040
Ala Glu Gln Leu Lys Val Ser Gln Thr Tyr Ser Lys Asn His Asp Ser
                1045                1050                1055
Gly Gly Val Ile Phe Ala Ser Ile Val Asn Phe Ser Glu Phe Tyr Glu
        1060                1065                1070
Glu Asn Tyr Glu Gly Gly Lys Glu Cys Tyr Arg Val Leu Asn Glu Leu
        1075                1080                1085
Ile Gly Asp Phe Asp Glu Leu Leu Ser Lys Pro Asp Tyr Asn Ser Ile
        1090                1095                1100
Glu Lys Ile Lys Thr Ile Gly Ala Thr Tyr Met Ala Ala Ser Gly Leu
1105                1110                1115                1120
Asn Thr Ala Gln Cys Gln Glu Gly Gly His Pro Gln Glu His Leu Arg
                1125                1130                1135
Ile Leu Phe Glu Phe Ala Lys Glu Met Met Arg Val Val Asp Asp Phe
        1140                1145                1150
Asn Asn Asn Met Leu Trp Phe Asn Phe Lys Leu Arg Val Gly Phe Asn
        1155                1160                1165
His Gly Pro Leu Thr Ala Gly Val Ile Gly Thr Thr Lys Leu Leu Tyr
        1170                1175                1180
Asp Ile Trp Gly Asp Thr Val Asn Ile Ala Ser Arg Met Asp Thr Thr
1185                1190                1195                1200
Gly Val Glu Cys Arg Ile Gln Val Ser Glu Glu Ser Tyr Arg Val Leu
                1205                1210                1215
Ser Lys Met Gly Tyr Asp Phe Asp Tyr Arg Gly Thr Val Asn Val Lys
        1220                1225                1230
Gly Lys Gly Gln Met Lys Thr Tyr Leu Tyr Pro Lys Cys Thr Asp Asn
        1235                1240                1245
```

```
-continued

Gly Val Val Pro Gln His Gln Leu Ser Ile Ser Pro Asp Ile Arg Val
    1250            1255                1260

Gln Val Asp Gly Ser Ile Gly Arg Ser Pro Thr Asp Glu Ile Ala Asn
1265            1270                1275                1280

Leu Val Pro Ser Val Gln Tyr Ser Asp Lys Ala Ser Leu Gly Ser Asp
                1285                1290                1295

Asp Ser Thr Gln Ala Lys Glu Ala Arg Leu Ser Ser Lys Arg Ser Trp
            1300                1305                1310

Arg Glu Pro Val Lys Ala Glu Glu Arg Phe Pro Phe Gly Lys Ala Ile
        1315                1320                1325

Glu Lys Asp Ser Cys Glu Asp Ile Gly Val Glu Glu Ala Ser Glu Leu
    1330                1335                1340

Ser Lys Leu Asn Val Ser Lys Ser Val
1345                1350
```

METHOD FOR IDENTIFYING CANDIDATE COMPOUNDS THAT BIND TO A HUMAN TYPE IX ADENYLYL CYCLASE POLYPEPTIDES

RELATED APPLICATIONS

This application is a divisional of U.S. patent application Ser. No. 10/071,223, filed Feb. 11, 2002 now U.S. Pat. No. 6,841,372, which is a divisional of U.S. patent application Ser. No. 09/473,717, filed Dec. 29, 1999, now U.S. Pat. No. 6,372,475, which is a continuation of International Application Ser. No. PCT/US98/13541, filed Jul. 1, 1998, which designated the U.S. and claims priority to U.S. Non-Provisional Application 08/886,440, filed Jul. 1, 1997, which has been converted to U.S. Provisional Application Ser. No. 60/098,559, filed Jul. 1, 1997, now abandoned, all of which are herein incorporated in their entirety.

FIELD OF THE INVENTION

This invention relates to DNA encoding a human adenylyl cyclase. This invention also relates to the adenylyl cyclase encoded by that DNA. Referred to herein as the human type IX adenylyl cyclase (hAC9) polypeptide, this enzyme can be used as a tool to screen for agonists and antagonists that can either stimulate or inhibit type IX adenylyl cyclase activity. Such compounds have therapeutic utility in treating (1) diseases that are caused by aberrant activity of this enzyme and (2) diseases whose symptoms can be ameliorated by stimulating or inhibiting the activity of type IX adenylyl cyclase.

The present invention also relates to the isolated entire human gene encoding the human type IX adenylyl cyclase, methods for the recombinant production of purified human type IX adenylyl cyclase and the proteins made by these methods, antibodies against the whole human type IX adenylyl cyclase or regions thereof, vectors, nucleotide probes, and host cells transformed by genes encoding polypeptides having human type IX adenylyl cyclase activity, along with diagnostic and therapeutic uses for these various reagents.

BACKGROUND OF THE INVENTION

Adenylyl cyclases direct the intracellular synthesis of the primary second messenger, cyclic-3',5'-adenosine monophosphate (cAMP), by converting ATP to cAMP, principally in response to a diverse family of membrane spanning, G-protein coupled receptors, each activated by its own extracellular hormone or protease. Signal transduction for G-protein coupled receptors occurs through a coupled heterotrimeric G protein complex composed of the alpha ($G_\alpha$), and beta/gamma ($G_{\beta\gamma}$) subunits. Upon receptor stimulation, $G_\alpha$ exchanges GTP for GDP, dissociates from both $G_{\beta\gamma}$ and the receptor, and proceeds to directly regulate various effectors, including adenylyl cyclase. Multiple families of $G_\alpha$ proteins have been identified, two of which are named for their effects on regulating adenylyl cyclase activity ($G_{\alpha s}$ family stimulates all adenylyl cyclases, while $G_{\alpha i}$ family inhibits most but not all of the adenylyl cyclases). Each of these $G_\alpha$ proteins has its own tissue distribution, and subset of coupled receptors, which favors receptor specific regulation of adenylyl cyclase.

Additional studies have suggested other means by which adenylyl cyclase activity may be regulated within tissues. This concept is derived from findings that a number of adenylyl cyclase isoforms exist, each with their own gene locus, distinct set of responses to intracellular signals and unique tissue distribution. To date, nine separate isoforms (Types I-IX) have been characterized, principally from rodents, each with its own regulatory properties and tissue specific distribution.

The structure of adenylyl cyclases has been greatly studied and the putative domains given standard nomenclature. Topographically, the adenylyl cyclase isoforms are similar, having two six-transmembrane spanning regions associated with an intracellular N-terminus, a large cytoplasmic loop (ICD III, more commonly referred to as "$C_1$") and a large intracellular C-terminus (more commonly referred to as "$C_2$"). The transmembrane region between the N-terminus and the $C_1$ loop is commonly referred to as "M1". The M1 region has three extracellular domains (ECD I, II and III), two intracellular domains (ICD I and II) and six transmembrane domains (TM I, II, III, V and VI). The region between the $C_1$ loop and the C-terminus is referred to as "M2". The M2 region has three extracellular domains (ECD IV, V and VI), two intracellular domains (ICD IV and V) and six transmembrane domains (TM VII, VIII, IX, X, XI and XII). The N-terminus is commonly divided into two regions, designated "$N_1$" and "$N_2$". The large $C_1$ cytoplasmic loop is also divided into two regions, a long "$C_{1a}$" region and a shorter "$C_{1b}$" region. Lastly, the C-terminus is divided into a long "$C_{2a}$" region and a shorter "$C_{2b}$" region. An extensive discussion of these regions can be found in Broach, et al., WO 95/30012, which is incorporated herein by reference. The amino acid sequence of the $C_{1a}$ and $C_{2a}$ regions are conserved among the different isoforms. On the other hand, the N-terminus, $C_{1b}$ and $C_{2b}$ regions show the most diversity among the various isoforms.

Based on sequence and functional similarities, these isoforms fall into six distinct classes of adenylyl cyclases. Types IV and VI have a wide tissue distribution.

However, Type IX is in a class of its own, being the most divergent of the isoforms and having a ubiquitous tissue distribution.

Diversity in activities, and differences in distribution and prevalence of adenylyl cyclase isoforms, may contribute to tissue specific regulation of cAMP levels. It is expected that by taking advantage of distinct structural and biochemical differences between different adenylyl cyclases, isoform specific or selective modulators can be discovered. This, in conjunction with knowledge of the proportion and distribution of each isoform in select tissues provides a means by which one can develop either tissue specific, or selective pharmacological agents since it is expected that isoform specific modulators would have tissue specificity related to the distribution of that isoform.

Key to the development of selective pharmacological agents is information pertaining to the tissue specific distribution and prevalence of each isoform. To date most of this information is available for isoform mRNA levels in a handful of non-human mammals, although some select mRNA (e.g. Type V) have been measured for many human tissues. Acquiring information on protein isoform distribution in human tissues is considered an important aspect of pharmaceutical research in this area, since this could either strengthen existing target information or point to different isoforms, when compared with mRNA data.

To date, only three full length human adenylyl cyclase isoforms have been cloned: Type II adenylyl cyclase (Stengel, et al., *Hum. Genet.* 90: 126-130 (1992)), Type VII adenylyl cyclase (Nomura, et al., *DNA Research* 1:27-35 (1994)) and Type VIII adenylyl cyclase (Defer, et al., *FEBS Letters* 351:109-113 (1994)).

Type IX, first cloned from mouse brain, is in a unique isoform class, being the most divergent of the isoforms and having a wide tissue distribution. Premont, et al. *Jour. Biol. Chem.* 271(23):13900-13907 (1996). The human isoform has not been cloned until now.

SUMMARY OF THE INVENTION

One aspect of the invention is an isolated and purified human type IX adenylyl cyclase (hAC9) polypeptide comprising the amino acid sequence of FIG. 2 (SEQ ID NO:2).

Another aspect of the invention is an isolated and purified nucleic acid encoding for the hAC9 polypeptide.

Yet another aspect of the invention is an isolated and purified nucleic acid comprising the nucleotide sequence of FIG. 2 (SEQ ID NO:1), which encodes a biologically active hAC9 polypeptide, or fragment thereof.

Still another aspect of the invention is an isolated and purified nucleic acid comprising the nucleotide sequence of FIG. 2 (SEQ ID NO:1), which encodes a biologically active soluble hAC9 peptide fragment.

Another aspect of the present invention also relates to the human gene encoding human type IX adenylyl cyclase, which has both diagnostic and therapeutic uses as are described below. Included within this invention are proteins or peptides having substantial homology with proteins or peptides comprising the amino acid sequence of FIG. 2 or encoded by a gene having substantial homology with the nucleotide sequence of FIG. 2, and which exhibit the same characteristics of human type IX adenylyl cyclase.

Yet another aspect of the invention is a method of producing hAC9 which comprises incorporating a nucleic acid having the nucleotide sequence of FIG. 2 (SEQ ID NO:1) into an expression vector, transforming a host cell with the vector and culturing the transformed host cell under conditions which result in expression of the gene.

BRIEF DESCRIPTION OF THE DRAWINGS

FIG. 1(A-C) is a partial restriction map and the cDNA clone of the human type IX heart adenylyl cyclase. FIG. 1A shows the nucleotide scale. FIG. 1B shows a partial restriction map of adenylyl cyclase cDNA. The coding portion is boxed and a hatched box shows the polyadenylation site. (ATG, a translation initiation codon, and TAG, a translation termination codon are shown, along with the restriction enzymes) FIG. 1C shows three cDNA clones, numbered 52, 10 and 5, obtained either from human heart lambda gt 10 cDNA libraries or by PCR.

FIG. 2(A-I) is the DNA (SEQ ID NO:1) and deduced amino acid sequence (SEQ ID NO:2) of human type IX adenylyl cyclase. The entire coding sequence, as well as portions of the 5' and 3' untranslated sequences, are shown. The whole sequence was done bidirectionally twice by dideoxy sequencing method using Taq polymerase.

FIG. 3(A-D) is a comparison of the amino acid sequence of the hAC9 polypeptide (SEQ ID NO:2) with the amino acid sequence of the murine type IX adenylyl cyclase (Premont, et al., supra) (SEQ ID NO:3).

DETAILED DESCRIPTION OF THE INVENTION

Definitions

Figure 4:
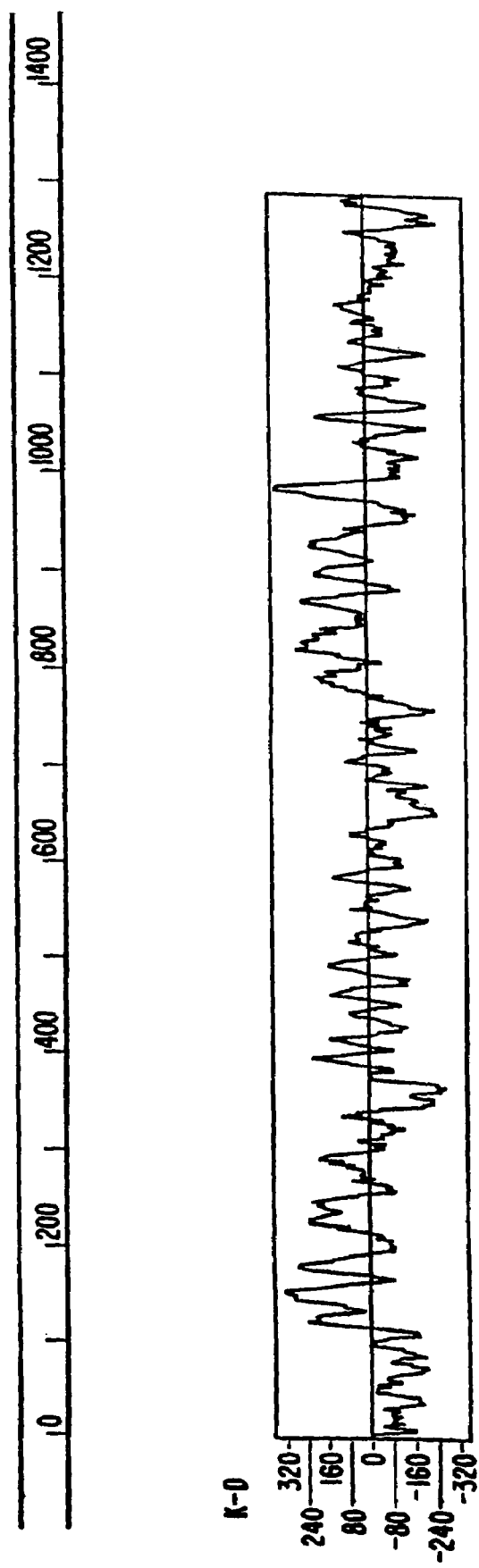
FIG. 4 shows a hydropathy plot of the hAC9 polypeptide. GeneVector 4.5 software was used to analyze the membrane related structure of hAC9. The method of Kyte, et al., *J. Mol. Bio.* 157:105-132 (1982) was used with a window size of 5.

Before proceeding further with a description of the specific embodiments of the present invention, a number of terms will be defined:

The terms "substantially pure" and "isolated" are used herein to describe a protein that has been separated from the native contaminants or components that naturally accompany it. Typically, a monomeric protein is substantially pure when at least about 60 to 70% of a sample exhibits a single polypeptide backbone. Minor variants or chemical modifications typically share approximately the same polypeptide sequence. A substantially pure protein will typically comprise over about 85 to 90% of a protein sample, preferably will comprise at least about 95%, and more preferably will be over about 99% pure. Purity is typically measured on a polyacrylamide gel, with homogeneity determined by staining. For certain purposes, high resolution will be desired and HPLC or a similar means for purification utilized. However, for most purposes, a simple chromatography column or polyacrylamide gel will be used to determine purity. Whether soluble or membrane bound, the present invention provides for substantially pure preparations. Various methods for their isolation from biological material may be devised, based in part upon the structural and functional descriptions contained herein. In addition, a protein that is chemically synthesized or synthesized in a cellular system that is different from the cell from which it naturally originates, will be substantially pure. The term is also used to describe proteins and nucleic acids that have been synthesized in heterologous mammalian cells, bacterial cells such as *E. coli* and other prokaryotes.

As used herein, the terms "hybridization" (hybridizing) and "specificity" (specific for) in the context of nucleotide sequences are used interchangeably. The ability of two nucleotide sequences to hybridize to each other is based upon a degree of complementarity of the two nucleotide sequences, which in turn is based on the fraction of matched complementary nucleotide pairs. The more nucleotides in a given sequence that are complementary to another sequence, the greater the degree of hybridization of one to the other. The degree of hybridization also depends on the conditions of stringency which include temperature, solvent ratios, salt concentrations, and the like. In particular, "selective hybridization" pertains to conditions in which the degree of hybridization of a polynucleotide of the invention to its target would require complete or nearly complete complementarity. The complementarity must be sufficiently high so as to assure that the polynucleotide of the invention will bind specifically to the target relative to binding other nucleic acids present in the hybridization medium. With selective hybridization, complementarity will be 90-100%, preferably 95-100%, more preferably 100%.

"Stringent conditions" are those that (1) employ low ionic strength and high temperature for washing, for example, 0.015 M NaCl/0.0015 M sodium titrated 0.1% NaDodSO$_4$ at 50° C., or (2) employ during hybridization a denaturing agent such as formamide, for example, 50% (vol/vol) formamide with 0.1% bovine serum albumin ("BSA")/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×0.75 M NaCl and 0.075 M sodium citrate ("SSC"), 50 mM sodium phosphate (pH 6.8), 0.1% sodium pyrophosphate, 5×

Denhardt's solution, sonicated salmon sperm DNA (50 mg/ml), 0.1% sodium dodecyl sulfate ("SDS"), and 10% dextran sulfate at 42° C., with washes at 42° C. in 0.2×SSC and 0.1% SDS.

"Isolated" nucleic acid will be nucleic acid that is identified and separated from contaminant nucleic acid encoding other polypeptides from the source of nucleic acid. The nucleic acid may be labeled for diagnostic and probe purposes, using any label known and described in the art as useful in connection with diagnostic assays.

PREFERRED EMBODIMENTS

The present invention relates to human type IX adenylyl cyclase, which is referred to herein as "hAC9". FIG. 2 shows the DNA sequence of the clone encoding the hAC9 polypeptide along with the deduced amino acid sequence. As used herein, the terms "hAC9 polypeptide" or "hAC9 enzyme" refer to any adenylyl cyclase sharing a common biological activity with the human type IX adenylyl cyclase contained in the clone described in Example 1. This "common biological activity" includes but is not limited to an effector function or cross-reactive antigenicity.

As indicated above, type IX adenylyl cyclase is in a unique isoform class, being the most divergent of the isoforms and having a wide tissue distribution. However, Type IX, as with the other known isoforms, has a similar putative structure: six extracellular domains; five intracellular domains, four small ones and a large cytoplasmic loop; and intracellular ammo and carboxy termini.

However, type IX adenylyl cyclase is distinguishable over other adenylyl cyclase isoforms in that it is larger than the other isoforms, in particular in the $C_{1b}$ and $C_{2b}$ regions. Further, type IX adenylyl cyclase is more ubiquitous than the other isoforms, being expressed in all tissues studied, both at the mRNA and protein level. Premont, et al., supra. In the other mammalian isoforms (types I-VIII), much of the membrane associated secondary structure is well conserved. Certain portions of the hAC9 polypeptide are similarly conserved. However, the hAC9 polypeptide is divergent in areas that are generally conserved in types I though VIII, making type IX the most divergent of the known isoforms.

Species variations between the human and murine type IX adenylyl cyclases rest predominantly in the C2b region.

The scope of the present invention is not limited to the exact sequence of the hAC9 cDNA set forth in FIG. 2 (SEQ ID NO: 1), or the use thereof. The invention contemplates certain modifications to the sequence, including deletions, insertions, and substitutions, such as are well known to those skilled in the art. For example, the invention contemplates replacing one or more codons in the cDNA sequence of FIG. 2, with codons that encode amino acids that are chemically equivalent to the amino acids in the native protein. Chemical equivalency is determined, for example, by one or more of the following characteristics: hydrophobicity or hydrophilicity, charge, size, whether the residue is cyclic or non-cyclic, aromatic or non-aromatic. So, for example, a codon encoding a neutral polar amino acid can be substituted with another codon that encodes a neutral polar residue, with the reasonable expectation of producing a biologically equivalent product.

Amino acid residues can be generally classified into four groups. Acidic residues are hydrophilic and have a negative charge due to loss of $H^+$ at physiological pH. Basic residues are also hydrophilic but have a positive charge due to association with $H^+$ at physiological pH. Neutral nonpolar residues are hydrophobic and are not charged at physiological pH. Neutral polar residues are hydrophilic and are not charged at physiological pH. Amino acid residues can be further classified as cyclic or noncyclic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic.

Of the naturally occurring amino acids, aspartic acid and glutamic acid are acidic; arginine and lysine are basic and noncyclic; histidine is basic and cyclic; glycine, serine and cysteine are neutral, polar and small; alanine is neutral, nonpolar and small; threonine, asparagine and glutamine are neutral, polar, large and nonaromatic; tyrosine is neutral, polar, large and aromatic; valine, isoleucine, leucine and methionine are neutral, nonpolar, large and nonaromatic; and phenylalanine and tryptophan are neutral, nonpolar, large and aromatic. Proline, although technically neutral, nonpolar, large, cyclic and nonaromatic, is a special case due to its known effects on the secondary conformation of peptide chains, and is not, therefore, included in this defined group.

There are also commonly encountered amino acids, which are not encoded by the genetic code. These include, by way of example and not limitation: sarcosine, beta-alanine, 2,3-diamino propionic and alpha-aminisobutyric acid which are neutral, nonpolar and small; t-butylalanine, t-butylglycine, N-methylisoleucine, norleucine and cyclohexylalanine which are neutral, nonpolar, large and nonaromatic; ornithine which is basic and noncyclic; cysteic acid which is acidic; citrulline, acetyl lysine, and methionine sulfoxide which are neutral, polar, large and nonaromatic; and phenylglycine, 2-naphthylalanine, β-2-thienylalanine and 1,2,3,4-tetrahydroisoquinoline-3-carboxylic acid which are neutral, nonpolar, large and aromatic.

Ordinarily, the hAC9 polypeptide claimed herein will have an overall amino acid sequence having at least 75% amino acid sequence identity with the hAC9 sequence disclosed in FIG. 2, more preferably at least 80%, even more preferably at least 90%, and most preferably at least 95%. More particularly, the N-terminus, $C_{1b}$ and $C_{2b}$ regions of the hAC9 polypeptide or polypeptide fragment claimed herein, will have an amino acid sequence having at least 90%, and most preferably at least 95% amino acid sequence identity with the hAC9 sequence disclosed in FIG. 2. Identity or homology with a sequence is defined herein as the percentage of amino acid residues in the candidate sequence that are identical with the sequence of the hAC9 polypeptide, after aligning the sequences and introducing gaps, if necessary, to achieve the maximum percent homology, and not considering any conservative substitutions as part of the sequence identity. N-terminal, C-terminal or internal extensions, deletions, or insertions of the hAC9 sequence shall be construed as affecting homology.

Thus, the claimed hAC9 polypeptide that is the subject of this invention includes molecules having the hAC9 amino acid sequence; fragments thereof having a consecutive sequence of at least 10, 15, 20, 25, 30 or 40 amino acid residues from the hAC9 sequence of FIG. 2, which exhibits the hAC9 polypeptide characteristics; amino acid sequence variants of the hAC9 sequence of FIG. 2 wherein an amino acid residue has been inserted N- or C-terminal to, or within, (including parallel deletions) the hAC9 sequence or its fragments as defined above; amino acid sequence variants of the hAC9 sequence of FIG. 2 or its fragments as defined above which have been substituted by at least one residue, and which exhibit the hAC9 polypeptide characteristics. Of particular interest are those peptides corresponding to those regions where the hAC9 polypeptide is divergent from types I though VIII.

Human type IX adenylyl cyclase polypeptides include those containing predetermined mutations by, e.g., homologous recombination, site-directed or PCR mutagenesis; naturally occurring variants of the hAC9 polypeptide; derivatives of the hAC9 polypeptide or its fragments wherein the hAC9 or its fragments have been covalently modified by substitution, chemical, enzymatic, or other appropriate means with a moiety other than a naturally occurring amino acid (for example a detectable moiety such as an enzyme or radioisotope); glycosylation variants of the hAC9 (insertion of a glycosylation site or deletion of any glycosylation site by deletion, insertion or substitution of appropriate amino acid); and soluble forms of the hAC9 polypeptide or fragments thereof. This invention also includes tagging the hAC9 polypeptide, for example, for use in a diagnostic application. Types and methods of tagging are well known in the art, for example, the use of hexa-histidine tags.

Other than the N-terminus, $C_1$ region and C-terminus of the hAC9 polypeptide, most regions of the Type IX isoform are highly conserved with the other adenylyl cyclase isoforms. Accordingly, it is believed that most sequence modifications to the highly conserved regions such as the extracellular domains, transmembrane regions and short intracellular domains, including deletions and insertions, and substitutions in particular, are not expected to produce radical changes in the characteristics of the hAC9 polypeptide, distinct from those found with similar changes to other isoforms. However, when it is difficult to predict the exact effect of the sequence modification in advance of making the change, one skilled in the art will appreciate that the effect of any sequence modification will be evaluated by routine screening assays.

The nomenclature used to describe the peptide compounds of the invention follows the conventional practice where the N-terminal amino group is assumed to be to the left and the carboxy group to the right of each amino acid residue in the peptide. In the formulas representing selected specific embodiments of the present invention, the amino- and carboxy-terminal groups, although often not specifically shown, will be understood to be in the form they would assume at physiological pH values, unless otherwise specified. Thus, the N-terminal $H^+_2$ and C-terminal $O^-$ at physiological pH are understood to be present though not necessarily specified and shown, either in specific examples or in generic formulas. Free functional groups on the side chains of the amino acid residues can also be modified by amidation, acylation or other substitution, which can, for example, change the solubility of the compounds without affecting their activity. All of the compounds of the invention, when an amino acid forms the C-terminus, may be in the form of the pharmaceutically acceptable salts or esters. Salts may be, for example, $Na^+$, $K^+$, $Ca^{+2}$, $Mg^{+2}$ and the like; the esters are generally those of alcohols of 1-6 carbons.

In all of the peptides of the invention, one or more amide linkages (—CO—NH—) may optionally be replaced with another linkage which is an isostere such as —CH$_2$NH—, —CH$_2$S—, —CH$_2$CH$_2$, —CH═CH— (cis and trans), —COCH$_2$—, —CH(OH)CH$_2$— and —CH$_2$SO—This replacement can be made by methods known in the art. The following references describe preparation of peptide analogs which include these alternative-linking moieties: Spatola, *Vega Data* 1(3) "Peptide Backbone Modifications" (general review) (March 1983); Spatola, in "Chemistry and Biochemistry of Amino Acids Peptides and Proteins," B. Weinstein, eds., Marcel Dekker, New York, p. 267 (1983) (general review); Morley, J. S., *Trends Pharm Sci*, pp. 463-468 (general review) (1980); Hudson, et al., *Int J Pept Prot Res* 14:177-185 (—CH$_2$NH—, —CH$_2$CH$_2$—) (1979); Spatola, et al., *Life Sci* 38:1243-1249 (—CH$_2$—S) (1986); Hann, *J Chem Soc Perkin Trans I* 307-314 (—CH—CH—, cis and trans) (1982); Almquist, et al., *J Med Chem* 23:1392-1398 (—COCH$_2$—) (1980); Jennings-White, et al., *Tetrahedron Lett* 23:2533 (—COCH$_2$—) (1982); Szelke, er al., European Application EP 45665 (1982) CA:97:39405 (1982) (—CH (OH)CH$_2$—); Holladay, et al., *Tetrahedron Lett* 4:4401-4404 (—C(OH)CH$_2$—) (1983); and Hruby, *Life Sci* 31:189-199 (—CH$_2$—S—) (1982).

Human type IX adenylyl cyclase peptides may be purified using techniques of classical protein chemistry, such as are well known in the art. For example, a lectin affinity chromatography step may be used, followed by a highly specific ligand affinity chromatography procedure that utilizes a ligand conjugated to biotin through the cysteine residues of the ligand. Alternately, the hexa-histidine tagged hAC9 polypeptide may be purified using nickel column chromatography.

One embodiment of the invention relates to recombinant materials associated with the production of the hAC9 polypeptide. One method of producing hAC9 comprises incorporating a nucleic acid having the nucleotide sequence of FIG. 2 (SEQ ID NO:1) into an expression vector, transforming a host cell with the vector and culturing the transformed host cell under conditions which result in expression of the gene. Suitable expression vectors include pc3hAC9. Examples of host cells includes bacterial, viral, yeast, insect or mammalian cell lines. A preferred host cell is the human embryonic cell line referred to as "HEK-293".

The invention also contemplates the use of transfected cells that can be cultured so as to display or express hAC9 on its surface, thus providing an assay system for the interaction of materials with the native hAC9 where these cells or relevant fragments of hAC9 are used as a screening tool to evaluate the effect of various candidate compounds on hAC9 activity in vivo, as is described below. Another embodiment of the invention relates to recombinant materials associated with the production of soluble hAC9 fragments. These include transfected cells, such as *E. coli*, that can be cultured so as to express active portions of the hAC9 polypeptide, in particular the C1 and C2 (C-terminus) intracellular loops. These soluble fragments can be purified and reconstituted to obtain enzymatic activity. This has been demonstrated with like domains from other isoforms. See Whisnant, et al., *Proc. Natl. Acad. Sci.*:93:6621-6625 (1996). Such soluble fragments can also be used as a screening tool to evaluate the effect of various candidate compounds on hAC9 activity. Suitable cells for transfection include bacterial cells, insect cells such as Sf-9 cells, yeast cells and most mammalian cell lines.

Recombinant production of the hAC9 polypeptide involves using a nucleic acid sequence that encodes hAC9, as is set forth in FIG. 2, or its degenerate analogs. The nucleic acid can be prepared either by retrieving the native sequence, as described below, or by using substantial portions of the known native sequence as a probe, or it can be synthesized de novo using procedures that are well known in the art.

The nucleic acid may be ligated into expression vectors suitable for the desired host and then transformed into compatible cells. Suitable vectors suitable for use in transforming bacterial cells are well known in the art. Plasmids and bacteriophages, such as lambda phage, are commonly used as vectors for bacterial hosts such as *E. coli*. Virus vectors are suitable for use in mammalian and insect cells for expression of exogenous DNA. Mammalian cells are readily transformed with SV40 or polyoma virus; and insect cells in culture may be transformed with baculovirus expression vectors. Suitable yeast vector systems include yeast centromere plasmids, yeast episomal plasmids and yeast integrating plasmids. Alternatively, nucleic acids may be introduced directly into a host cell by techniques such as are well known in the art.

The cells are cultured under conditions favorable for the expression of the gene encoding the hAC9 polypeptide and cells displaying hAC9 on the surface are then harvested. Suitable eukaryotic host cells include mammalian cells, plant cells, yeast cells and insect cells. Suitable prokaryotic host cells, include bacterial cells such as *E. coli* and *Bacillus subtilis*, Chinese Hamster Ovary cells, COS cells, the rat-2 fibroblast cell line, the human embryonic kidney 293 cell line, and insect cell lines such as Sf-9.

This invention also relates to nucleic acids that encode or are complementary to a hAC9 polypeptide. These nucleic acids can then be used to produce the polypeptide in recombinant cell culture for diagnostic use or for potential therapeutic use. In still other aspects, the invention provides an isolated nucleic acid molecule encoding hAC9, either labeled or unlabeled, or a nucleic acid sequence that is complementary to, or hybridizes under stringent conditions to, a nucleic acid sequence encoding hAC9. The isolated nucleic acid molecule of the invention excludes nucleic acid sequences which encode, or are complementary to nucleic acid sequences encoding, other known adenylyl cyclase isoforms.

This invention also provides a replicable vector comprising a nucleic acid molecule encoding hAC9 operably linked to control sequences recognized by a host transformed by the vector; host cells transformed with the vector; and a method of using a nucleic acid molecule encoding hAC9 to effect the production of hAC9 on the cell surface or as soluble fragments, comprising expressing the nucleic acid molecule in a culture of the transformed host cells and recovered from the cells. The nucleic acid sequence is also useful in hybridization assays for hAC9-encoding nucleic acid molecules.

In still further embodiments of the invention, a method is described for producing hAC9 comprising inserting into the DNA of a cell containing the nucleic acid sequence encoding hAC9, a transcription modulatory element (such as an enhancer or a silencer) in sufficient proximity and orientation to the hAC9-coding sequence to influence transcription thereof, with an optional further step comprising culturing the cell containing the transcription modulatory element and the hAC9-encoding nucleic acid sequence.

This invention also covers a cell comprising a nucleic acid sequence encoding the hAC9 polypeptide and an exogenous transcription modulatory element in sufficient proximity and orientation to the above coding sequence to influence transcription thereof and a host cell containing the nucleic acid sequence encoding hAC9 operably linked to exogenous control sequences recognized by the host cell.

This invention provides a method for obtaining cells having increased or decreased transcription of the nucleic acid molecule encoding the hAC9 polypeptide, comprising: providing cells containing the nucleic acid molecule; introducing into the cells a transcription modulating element; and screening the cells for a cell in which the transcription of the nucleic acid molecule is increased or decreased.

Human adenylyl cyclase type IX nucleic acids for use in the invention can be produced as follows. A hAC9 "nucleic acid" is defined as RNA or DNA that encodes the hAC9 polypeptide, or is complementary to nucleic acid sequence encoding hAC9, or hybridizes to such nucleic acid and remains stably bound to it under stringent conditions, or encodes a polypeptide sharing at least 75% sequence identity, preferably at least 80%, and more preferably at least 85%, with the deduced amino acid sequence shown in FIG. 2. It is typically at least about 10 nucleotides in length and preferably has hAC9 related biological or immunological activity. Specifically contemplated are genomic DNA, cDNA, mRNA and antisense molecules, as well as nucleic acids based on alternative backbone or including alternative bases whether derived from natural sources or synthesized.

Of particular interest is a hAC9 nucleic acid that encodes a full-length molecule, including but not necessarily the native signal sequence thereof. Nucleic acid encoding full-length protein is obtained by screening selected cDNA or genomic libraries using the deduced amino acid sequence disclosed herein for the first time, and, if necessary, using conventional primer extension procedures to secure DNA that is complete at its 5' coding end. Such a clone is readily identified by the presence of a start codon in reading frame with the original sequence.

DNA encoding an amino acid sequence variant of the hAC9 polypeptide is prepared as described below or by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of hAC9.

Techniques for isolating and manipulating nucleic acids are disclosed for example by the following documents: U.S. Pat. No. 5,030,576, 5,030,576 and International Patent Publications WO94/11504 and WO93/03162. See, also, Sambrook, et al., "Molecular Cloning: A Laboratory Manual", 2nd Edition, Cold Spring Harbor Press, Cold Spring Harbor, N.Y., 1989, and Ausubel, et al. "Current Protocols in Molecular Biology", Vol. 2, Wiley-Interscience, New York, 1987.

The isolation, recombinant production and characterization of the hAC9 polypeptide allows for the design of assay systems using hAC9. The availability of the isolated cells providing hAC9 on their surface and the availability of the recombinant DNA encoding hAC9 which permits display and expression of the enzyme on host cell surfaces, all makes such cells available as a valuable tool for evaluating the ability of candidate pharmaceuticals, both agonists and antagonists, to affect the activity of hAC9. In this manner, the invention is related to assay systems which utilize isolated or recombinantly produced hAC9 to screen for agonist and antagonist activity of candidate drugs. This assay is especially useful in assuring that these candidate therapeutic agents have the desired effect on hAC9. Determination of these properties is essential in evaluating the specificity of drugs for other adenylyl cyclase isoforms.

The host cells are typically animal cells, most typically mammalian cells. In order to be useful in the assays, the cells must have intracellular mechanisms which permit hAC9 to be displayed on the cell surface or to be expressed as soluble fragments. The animal host cells expressing the DNA encoding the hAC9 polypeptide or a fragment thereof are then cultured to effect the expression of the encoding nucleic acids so as to either 1) produce hAC9 display on the cell surface such that the cells can then be used directly in assays for assessment of a candidate drug to bind to or otherwise affect the activity of the enzyme, or 2) produce hAC9 as soluble fragments which can then be purified and reconstituted to obtain an enzymatically active compound useful in screening assays.

There are several possible strategies to identify compounds which affect hAC9 activity. Over expression of the hAC9 cDNA can provide a means for isolation of large quantities of crude membrane preparations from a stable cell line. HEK-293 cells have been found to be particularly useful for this purpose. In this system the measurable enzyme activity would be predominantly from expression of recombinant hAC9. A highly sensitive, reproducible, high throughput screening system is desirable, with enzyme activity detected in a 96 well, scintillation proximity-type assay to measure product formation (cAMP). There are numerous screening assays that can be utilized. For example, the basal (unstimulated) activity of hAC9 can be measured as a method of detecting both agonists and antagonists of the hAC9 enzyme. In addition, stimulation of the enzyme by its most relevant physiological activator, the heterotrimeric G protein subunit, $G_{as}$, can be assayed using activated (GTPgS bound) recombinant bovine $G_{as}$ (expressed and purified from bacteria), with the expectation that additional compounds may be identified which inhibit $G_{as}$ stimulation of the hAC9 polypeptide. Other stimulatory agents can also be used, such as forskolin or forskolin analogs. "Hits", i.e., compounds which affect hAC9, in any of these screens will be further evaluated in other assays to help focus on compounds which are relevant to the targeted isoform.

Another method of evaluating candidates as potential therapeutic agents typically involves a screening based approach such as a binding assay in which the candidate (such as a peptide or a small organic molecule) would be tested to measure if, or to what extent, it binds the catalytic subunit of the hAC9 enzyme. Preferably, a mammalian cell line that expresses recombinant hAC9 or plasma membrane preparations thereof, will be used in the assay. For example, a candidate antagonist competes for binding to hAC9 with either a labeled agonist or antagonist, for example labeled forskolin or a labeled forskolin analog. Varying concentrations of the candidate are supplied, along with a constant concentration of the labeled agonist or antagonist. The inhibition of binding of the labeled material can then be measured using established techniques. This measurement is then correlated to determine the amount and potency of the candidate that is bound to hAC9.

Another method of identifying compounds which affect hAC9 activity is the rational design of synthetic compounds based on nucleotide scaffolds, targeted to either of two distinct sites on the hAC9 enzyme. One of these is the active site (ATP being the substrate, cAMP being the product) and the other is the separate P site (adenine nucleoside 3'-polyphosphates reportedly demonstrating the greatest inhibitory activity, with either pure or crude enzyme preparations). As a related approach, one could attempt to design forskolin analogues which may demonstrate isoform specific effects.

In addition, using the above assays, the ability of a candidate drug to stimulate or inhibit the activity of hAC9 can be tested directly.

Once lead candidates are identified, and for purposes of demonstrating that isoform specificity may be achieved with small molecule modulators, it is desirable to develop assay systems which monitor most, and preferably all, human adenylyl cyclase isoforms. These assays may be used to evaluate either existing (e.g. forskolin analogs or P site inhibitors) or newly discovered small molecule modulators and determine structure activity relationships for different adenylyl cyclase isoforms. Such assays could also be used to evaluate either specific or selective modulators of other adenylyl targets and with use of a whole cell assay, may provide useful insights for designing bioavailability and addressing biological activity of lead candidates.

The hAC9 also has utility in assays for the diagnosis of diseases and disorders by detection, in tissue samples, of aberrant expression of the hAC9 enzyme.

Another aspect of the invention relates to hAC9 agonists that imitate the naturally occurring form of hAC9. These agonists are useful as control reagents in the above-mentioned assays to verify the workability of the assay system. In addition, agonists for hAC9 may exhibit useful effects in vivo in treating disease.

Another aspect of the invention relates to hAC9 antagonists that are modified forms of hAC9 peptides. Such antagonists bind to hAC9, and prevent enzyme-substrate interaction by blocking their binding to hAC9. Another group of compounds within the scope of the invention, are antagonists of hAC9 substrate, i.e., these are substrate inhibitors. Both these types of antagonists find utility in diminishing or mediating events based upon enzyme-substrate interaction such as cAMP production. Yet another second group of antagonists includes antibodies designed to bind specific portions of hAC9. In general, these are monoclonal antibody preparations which are highly specific for any desired region of hAC9, although polyclonal antibodies are also contemplated by this invention. The antibodies, which are explained in greater detail below, are also useful in immunoassays for the hAC9 enzyme, for example, in assessing successful expression of the gene in recombinant systems.

In both the agonists and antagonists, a preferred embodiment is that class of compounds having amino acid sequences that are encoded by the hAC9 gene. The invention also includes those compounds where one, two, three or more of said amino acid residues are replaced by one(s) which is not encoded genetically. Also included in the invention are isolated DNA molecules that encode these specific peptides.

It is believed that the extracellular domains of enzymes may play a key role in extracellular activities, for example, in enzyme regulation. Accordingly, the invention includes agonists and antagonists having amino acid sequences, in whole or in part, corresponding to the extracellular domains of hAC9, the sequences of which can be approximated from the amino acid sequence of FIG. 2 and the hydropathy analysis of FIG. 4. Of particular interest is ECD VI, the largest of the extracellular domains, and ECD II and III, which are also relatively large domains. The invention also includes agonists and antagonists that affect the enzyme's function by binding to the N- or C-terminus or to one of the intracellular (ICD) domains of hAC9, the sequences of which can be approximated from the amino acid sequence of FIG. 2 and the hydropathy analysis of FIG. 4.

In other adenylyl cyclases, the ICD IV and carboxy terminus regions have been shown to play a role in enzyme activity or $G_\alpha$ or forskolin interaction. See for example: Whisnant, et al., supra. Accordingly, it is expected that the amino acid sequences of the ICD IV and carboxy terminus regions of hAC9, in whole or in part, will be particularly useful in designing antibodies or peptides that can bind the enzyme and block enzyme activity or $G_{as}$ interaction.

As the understanding of adenylyl cyclases and factors which effect isoform activity increases, rational drug design is becoming a viable alternative in pharmaceutical research. It is believed that the two conserved intracellular domains of adenylyl cyclase (the $C_1$ and $C_2$ domains) associate to form an active enzyme. This has been demonstrated with studies that combine both expressed recombinant $C_1$ and $C_2$ domains. Both the $C_1$ and $C_2$ domains are required to reconstitute enzyme activity while either alone has no substantial activity, Forskolin plus $G_{as}$ stimulates this system, by increasing the association of the two domains. Designing assays which monitor enzyme activity, dependent on association of two separate domains, is expected to provide greater sensitivity to antagonists since this would presumably be more easily disrupted. Other studies have demonstrated that peptides, comprised of sequences from conserved regions of the intracellular domains, act as inhibitors of detergent solubilized enzyme preparations. This invention contemplates the use of peptide walking strategies, to delimit regions of the modulator which may be responsible for its activity, leading to the design of small molecule inhibitors. Finally, knowledge of uncharacterized, physiological modulators of adenylyl cyclase, particularly those that demonstrate isoform specificity, may provide new assay systems for identifying novel AC modulators. It is expected that many of these modulators would be proteins and some may be identified while using adenylyl cyclase sequences as "bait" in a yeast two hybrid system. Alternatively one may identify proteins which coprecipitate with adenylyl cyclase upon capture with adenylyl cyclase antibodies.

The peptide agonists and antagonists of the invention are preferably about 10-100 amino acids in length, more preferably 25-75 amino acids in length. These peptides can be readily prepared using standard solid phase or solution phase peptide synthesis, as is well known in the art. In addition, the DNA encoding these peptides can be synthesized using commercially available oligonucleotide synthesis instrumentation and recombinantly produced using standard recombinant production systems. Production using solid phase peptide synthesis is required when non-gene encoded amino acids are to be included in the peptide.

Another aspect of the invention pertains to antibodies, which have both diagnostic and therapeutic uses. Antibodies are able to act as antagonists or agonists by binding specific regions of the hAC9 polypeptide. These antibodies also find utility in immunoassays that measure the presence of hAC9, for example in immunoassays that measure gene expression. In general, antibodies to adenylyl cyclases, and more importantly, those which may recognize specific isoforms of adenylyl cyclase, are a useful tool to evaluate tissue distribution and prevalence of the adenylyl cyclase protein. By identifying regions of dissimilarity between the adenylyl cyclase isoforms and the antigenic potential of these regions, either synthetic peptides or recombinant proteins to these sequences can be created for use in immunization. The resulting antibodies would then be characterized for specificity based on the unique qualities of the immunogen and reactivity with other expressed isoforms. Detection of isoform protein in various tissues can readily be monitored by Westerns blots; however, immunohistochemical analysis would also be useful. This information is useful to identify the adenylyl cyclase target of interest, providing valuable insights into useful therapeutic strategies such as targets in cardiovascular disease, asthma or obesity.

The antibodies of the present invention can be prepared by techniques that are well known in the art. The antibodies can be monoclonal or polyclonal, but are preferably monoclonal antibodies that are highly specific for hAC9 and can be raised against the whole hAC9 polypeptide or regions thereof. Antibodies are prepared by immunizing suitable mammalian hosts (typically rabbit, rat, mouse, goat, human, etc.) in appropriate immunization protocols using the peptide haptens (immunogen) alone, if they are of sufficient length, or, if desired, or if required to enhance immunogenicity, conjugated to suitable carriers. The immunogen will typically contain a portion of the hAC9 polypeptide that is intended to be targeted by the antibodies. Critical regions include those regions corresponding to the extracellular domains of the hAC9 enzyme, any region(s) of proteolytic cleavage, and any segment(s) of the extracellular segment critical for activation. Methods for preparing immunogenic conjugates with carriers such as bovine serum albumin, keyhole limpet hemocyanin, or other carrier proteins are well known in the art. In some circumstances, direct conjugation using for example, carbodiimide reagents may be effective; in other instances linking reagents such as those supplied by Pierce Chemical Co., Rockford, Ill., may be desirable to provide accessibility to the hapten. The hapten can be extended at the amino or carboxy terminus with a cysteine residue or interspersed with cysteine residues, for example, to facilitate linking to carrier. The desired immunogen is administered to a host by injection over a suitable period of time using suitable adjuvants followed by collection of sera. Over the course of the immunization schedule, titers of antibodies are taken to determine the adequacy of antibody formation.

Polyclonal antibodies are suitable for many diagnostic and research purposes and are easily prepared. Monoclonal antibodies are often preferred for therapeutic applications and are prepared by continuous hybrid cell lines and collection of the secreted protein. Immortalized cell lines that secrete the desired monoclonal antibodies can be prepared by the method described in Kohler and Milstein, *Nature* 256:495-497 (1975) or modifications which effect immortalization of lymphocytes or spleen cells, as is generally known. The immortalized cell lines are then screened by immunoassay techniques in which the antigen is the immunogen or a cell expressing hAC9 on its surface. Cells that are found to secrete the desired antibody, can then be cultured in vitro or by production in the ascites fluid. The antibodies are then recovered from the culture supernatant or from the ascites supernatant.

Alternately, antibodies can be prepared by recombinant means, i.e., the cloning and expression of nucleotide sequences or mutagenized versions thereof that at a minimum code for the amino acid sequences required for specific binding of natural antibodies. Antibody regions that bind specifically to the desired regions of hAC9 can also be produced as chimeras with regions of multiple species origin.

Antibodies may include a complete immunoglobulin or a fragment thereof, and includes the various classes and isotypes such as IgA, IgD, IgE, IgG1, IgG2a, IgG2b, IgG3 and IgM. Fragments include Fab, Fv, $F(ab')_2$, Fab', and so forth. Fragments of the monoclonals or the polyclonal antisera which contain the immunologically significant portion can be used as antagonists, as well as the intact antibodies. Use of immunologically reactive fragments, such as the Fab, Fab', or $F(ab')_2$ fragments is often preferable, especially in a therapeutic context, as these fragments have different immunogenicity than the whole immunoglobulin, and do not carry the biological activity of an immunoglobulin constant domain.

The antibodies thus produced are useful not only as potential agonist or antagonists for the hAC9 polypeptide, filling the role of agonist or antagonist in the assays of the invention, but are also useful in immunoassays for detecting the hAC9 enzyme. As such these antibodies can be coupled to imaging agents for administration to a subject to allow detection of localized antibody to ascertain the under-or over-expression of hAC9 in tissues of interest. In addition, these reagents are useful in vitro to detect, for example, the successful production of hAC9 on the surface of the recombinant host cells.

Yet another aspect of the invention relates to pharmaceutical compositions containing the compounds and antibodies of the invention. The agonists and antagonists of the invention have therapeutic utility in (1) treating diseases caused by aberrant activity of the hAC9 enzyme in tissues where it is customarily found, for example in the adrenal gland, heart or brain and (2) treating diseases whose symptoms can be ameliorated by stimulating or inhibiting the activity of hAC9.

The peptide agonists and antagonists of the invention can be administered in conventional formulations for systemic administration such as is well known in the art. Typical formulations may be found, for example, in *Remington's Pharmaceutical Sciences*, Mack Publishing Co., Easton Pa., latest edition.

Preferred forms of systemic administration include injection, typically by intravenous injection. Other injection routes, such as subcutaneous, intramuscular, or intraperitoneal, can also be used. More recently, alternative means for systemic administration of peptides have been devised which include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the patient's condition, and the judgment of the attending physician. Suitable dosage ranges, however, are in the range of 0.1-100 µg/kg of subject. Wide variations in the needed dosage, however, are to be expected in view of the variety of peptides available and the differing efficiencies of various routes of administration. For example, oral administration would be expected to require higher dosages than administration by intravenous injection. Variations in these dosage levels can be adjusted using standard empirical routines for optimization as is well understood in the art.

The invention also relates to the therapeutic, prophylactic and research uses of various techniques to block or modulate the expression of the hAC9 by interfering with the transcription of translation of a DNA or RNA molecule encoding the hAC9. This includes a method to inhibit or regulate expression of hAC9 in a cell comprising providing to the cell an oligonucleotide molecule which is antisense to, or forms a triple helix with, hAC9-encoding DNA or with DNA regulating expression of hAC9-encoding DNA, in an amount sufficient to inhibit or regulate expression of the hAC9, thereby inhibiting or regulating its expression. Also included is a method to inhibit or regulate expression of hAC9 in a subject, comprising administering to the subject an oligonucleotide molecule which is antisense to, or forms a triple helix with, hAC9-encoding DNA or with DNA regulating expression of hAC9-encoding DNA, in an amount sufficient to inhibit or regulate expression of hAC9 in the subject, thereby inhibiting or regulating its expression. The antisense molecule or triple helix-forming molecule in the above methods is preferably a DNA or RNA oligonucleotide. These utilities are described in greater detail below.

The constitutive expression of antisense RNA in cells has been shown to inhibit the expression of about 20 different genes in mammals and plants, and the list continually grows (Hambor, et al., *J. Exp. Med.* 168:1237-1245 (1988); Holt, et al., *Proc. Natl. Acad. Sci.* 83:4794-4798 (1986); Izant, et al., *Cell* 36:1007-1015 (1984); Izant, et al., *Science* 229: 345-352 (1985) and De Benedetti, et al., *Proc. Natl. Acad. Sci.* 84:658-662 (1987)). Possible mechanisms for the antisense effect are the blockage of translation or prevention of splicing, both of which have been observed in vitro. Interference with splicing allows the use of intron sequences (Munroe, *EMBO. J.* 7:2523-2532 (1988) which should be less conserved and therefore result in greater specificity in inhibiting expression of a protein of one species but not its homologue in another species.

Therapeutic gene regulation is accomplished using the "antisense" approach, in which the function of a target gene in a cell or organism is blocked, by transfection of DNA, preferably an oligonucleotide, encoding antisense RNA which acts specifically to inhibit expression of the particular target gene. The sequence of the antisense DNA is designed to result in a full or preferably partial antisense RNA transcript which is substantially complementary to a segment of the gene or mRNA which it is intended to inhibit. The complementarity must be sufficient so that the antisense RNA can hybridize to the target gene (or mRNA) and inhibit the target gene's function, regardless of whether the action is at the level of splicing, transcription or translation. The degree of inhibition, readily discernible by one of ordinary skill in the art without undue experimentation, must be sufficient to inhibit, or render the cell incapable of expressing, the target gene. One of ordinary skill in the art will recognize that the antisense RNA approach is but one of a number of known mechanisms which can be employed to block specific gene expression.

By the term "antisense" is intended an RNA sequence, as well as a DNA sequence coding therefor, which is sufficiently complementary to a particular mRNA molecule for which the antisense RNA is specific to cause molecular hybridization between the antisense RNA and the mRNA such that translation of the mRNA is inhibited. Such hybridization must occur under in vivo conditions, that is, inside the cell. The action of the antisense RNA results in specific inhibition of gene expression in the cell. See Albers, et al., "Molecular Biology Of The Cell", 2nd Ed., Garland Publishing, Inc., New York, N.Y. (1989), in particular, pages 195-196.

The antisense RNA of the present invention may be hybridizable to any of several portions of a target mRNA, including the coding sequence, a 3' or 5' untranslated region, or other intronic sequences. A preferred antisense RNA is that complementary to hAC9 mRNA. As is readily discernible by one of skill in the art, the minimal amount of homology required by the present invention is that sufficient to result in hybridization to the specific target mRNA and inhibition of its translation or function while not affecting function of other mRNA molecules and the expression of other genes.

Antisense RNA is delivered to a cell by transformation or transfection with a vector into which has been placed DNA encoding the antisense RNA with the appropriate regulatory sequences, including a promoter, to result in expression of the antisense RNA in a host cell.

"Triple helix" or "triplex" approaches involve production of synthetic oligonucleotides which bind to the major groove of a duplex DNA to form a colinear triplex. Such triplex formation can regulate and inhibit cellular growth. See, for example, Hogan, et al., U.S. Pat. No. 5,176,996; Cohen, et al., *Sci. Amer.*, December 1994, p. 76-82; Helene, *Anticancer Drug Design* 6:569-584 (1991); Maher III, et al., *Antisense Res. Devel.* 1:227-281 (Fall 1991); and Crook, et al. eds., "Antisense Research and Applications", CRC Press, 1993; all of which are incorporated herein by reference. It is based in part on the discovery that a DNA oligonucleotide can bind by triplex formation to a duplex DNA target in a gene regulatory region, thereby repressing transcription initiation (Cooney, et. al. *Science* 241:456 (1988)). The present invention utilizes methods such as those of Hogan et al., supra, to designing oligonucleotides which will bind tightly and specifically to a duplex DNA target comprising part of the hAC9-encoding DNA or a regulatory sequence thereof. Such triplex oligonucleotides can therefore be used as a class of drug molecules to selectively manipulate the expression of this gene.

Thus the present invention is directed to providing to a cell or administering to a subject a synthetic oligonucleotide in sufficient quantity for cellular uptake and binding to a DNA duplex of the target hAC9 coding DNA sequence or a regulatory sequence thereof, such that the oligonucleotide binds to the DNA duplex to form a colinear triplex. This method is used to inhibit expression of the hAC9 enzyme on cells in vitro or in vivo. Preferably the target sequence is positioned within the DNA domain adjacent to the RNA transcription origin. This method can also be used to inhibit growth of cells which is dependent on expression of this enzyme. The method may also be used to alter the relative amounts or proportions of the hAC9 expressed on cells or tissues by administering such a triplex-forming synthetic oligonucleotide.

The following examples are intended to illustrate but not to limit the invention.

EXAMPLE 1

Construction and Screening of a Human Heart cDNA Library

Whole human heart was used as a source of mRNA. The libraries were purchased from a commercial source, Clontech (Catalog No. HL3026a). The libraries were prepared in a lambda gt10 phage with both oligo-dT and random primers. The primary screening of the lambda gt10 library was carried out with gentle washing (less stringent conditions). Approximately 500,000 plaques were initially screened from the library. Prehybridization is carried out for at least 2 hours in a solution containing 500 mM NaHPO$_4$ (pH 7.2), 7% SDS, 1 mM EDTA (pH 8) and 1 mg/ml BSA at 65° C. Hybridization was then performed in the same solution at 65° C. A 295 base pair (bp) PCR fragment from type I adenylyl cyclase cDNA was used as a probe. This fragment encodes the $C_{1b}$ domain of the adenylyl cyclase, which has significant homology to other previously-known types of adenylyl cyclase.

The probe was radiolabeled with $^{32}$P-dCTP by the random primer labeling method. After hybridization for 16 hours, the blot was washed under increasingly stringent conditions and then radioautographed. One positive clone was obtained. The size of the insert in the clone was 4.55 kb (kilobases).

The next step was to ascertain the full length cDNA sequence from the inserts in the clones. All the positive clones from the human heart library were subcloned into plasmid pBluescript. After restriction maps were made, they were further subcloned and sequenced with universal primers or synthesized oligomers. The sequence was performed bidirectionally at least twice with Sequenase (Tabor, et al., *Proc. Natl. Acad. Sci. USA* 84:4767-4771 (1987).

A clone designated #52 was found to be of particular interest. After the entire coding portion of clone #52 was sequenced, it is found that it contained an insert of 4.55 kb with a polyadenylation signal at its 3' end (FIG. 1).

The sequence from the 5' end of clone #52 was used to generate PCR primers which were used to acquire a clone designated #10, by the PCR-based RACE ("rapid amplification of cDNA ends") technique (Frohman, M. A., *Methods Enzymol.* 218:340-362 (1991)) and human heart mRNA. Clone #10 did not contain an initiation ATG (See FIG. 1C) with a conserved Kozak consensus sequence, which provides a favorable context for initiating translation (Kozak, *Cell. Biol.* The entire clone #10 was used as a probe to screen a separate human heart library. Several clones were obtained. It was found that a clone designated #5 overlapped 2225 bases with clone #52, and extended the cDNA sequence up stream an additional 435 bp. After sequencing the whole insert, an ATG with conserved Kozak consensus sequence was found at its 5' end (ATG, FIG. 1). This open reading frame of 3882 bases reads through to a TGA, a translation termination codon (FIGS. 1 and 2). Thus, clones #52 and #5 encode a protein of 1294 amino acids. The entire coding portion of the cDNA and its deduced amino acid sequence are shown (FIG. 2) (SEQ ID NO: 1 and 2, respectively).

A 551 bp Hind III-MluI fragment from clone #5 and a 3596 bp MluI-SspI fragment from clone #52 was subcloned into pcDNA3, obtained from Invitrogen. The resulting expression vector, containing the full length cDNA, was designated pc3hAC9. Samples of this expression vector, inserted into an appropriate *E. coli* strain designated SURE, were deposited with the American Type Culture Collection, 1081 University Boulevard, Manassas. Va. 20110-2209, on Mar. 5, 2002 in accordance with the Budapest Treaty on the International Recognition of the Deposit of Microorganisms for the Purposes of Patent Procedure and have been accorded accession number ATCC PTA-3983.

EXAMPLE 2

Cloning an Expression of the Human Type IX Adenylyl Cyclase

The human type IX adenylyl cyclase was produced by cloning and expressing heart type IX adenylyl cyclase cDNA in a suitable expression system using recombinant DNA methods, such as are well known in the art.

4 µg of the purified plasmid pc3hAC9 were transfected into HEK-293 cells using electroporation. The cells were grown to approximately 80% confluency in DMEM:FR (50% Dulbecco's modified Eagle's Medium/50% F12, 10% fetal calf serum, 2 mM glutamine, 4.5 mg/ml glucose, 10 μg/ml streptomycin sulfate and 60 μg/ml penicillin K) ("Growth Media"). After washing with phosphate buffered saline ("PBS") twice, 0.5 ml of trypsin solution was added. The cells are incubated for 5 minutes, harvested and resuspended in Growth Media in 4 μl of water. 4 μg of purified plasmid was added to an electroporation cuvette. 0.4 ml of 25×10$^6$ cells/ml were added to the DNA and the mixture was pulsed at 960 μF, 0.241 kV. After 10 minutes the cell-DNA mixture was plated into Growth Media. The plate was incubated at 37° C. for 48 hours before placing cells on Selective Media (Growth Media, 1 mg/ml of the antibiotic, G-418).

hAC9, having 1294 amino acids, was analyzed for secondary structure by the method of Kyte, et al., supra (FIG. 4). The software, GeneWorks; v. 2.45; IntelliGenetics, Inc.; Mountain View; Calif. was used to obtain a hydropathy plot, shown in FIG. 4, and thereby identify the membrane related structure of this adenylyl cyclase isoform. The method of Kyte, et al., supra, was used with a window size of 5.

Twelve peaks appear in the hydropathy plot, which represent transmembrane spanning regions. These results suggest that this adenylyl cyclase isoform has a structure of twelve transmembrane spanning regions, as well as a large cytoplasmic loop located in the middle and at the end, which is consistent with the structures of the previously characterized isoforms. In the transmembrane positions, the sixth extracellular loop is the largest (between the eleventh and twelfth transmembrane spans).

EXAMPLE 3

Evaluation of the Human Type IX Adenylyl Cyclase

The biochemical characteristics of hAC9 were determined in a stable expression system using HEK-293 cells. A fragment of the adenylyl cyclase cDNA containing the whole coding sequence was inserted into the pc3hAC9 plasmid described above.

The following assay was performed to measure the adenylyl cyclase activity of a membrane which had been transfected with the expression vector pc3hAC9 carrying hAC9 cDNA. The transfected HEK-293 cells were washed twice with 150 mM NaCl and scraped in 2 ml of cold buffer containing 50 mM Tris (pH 7.4), 2 mM MgCl$_2$, 1 mM EDTA, 0.5 mM dithiothreitol ("DTT"), 0.5 mM phenylmethylsulfonylfluoride ("PMSF"), 0.5 (g/ml leupeptin, and 0.044 U/ml aprotinin on ice. The membrane was homogenated by 20 strokes in a Dounce homogenizer and was centrifuged at 600×g for 2 minutes at 4° C. The supernatant was further centrifuged at 30,000×g for 20 minutes at 4° C. The resultant pellet was resuspended in 50 mM Tris (pH 7.4), 2 mM MgCl$_2$, 1 mM EDTA, 0.5 mM DTT, 0.5 mM PMSF, 0.5 (g/ml leupeptin, and 0.044 U/ml aprotinin. This crude membrane solution was used for the adenylyl cyclase assay.

The adenylyl cyclase assay was performed by the method described by Salomon, *Adv. Cyclic Nucleotide Res.* 10:35-55 (1979). Crude membranes from the HEK-293 cells were resuspended in a solution containing 100 mM Tris (pH 7.4), 5 mM ATP, 5 mM (-mercaptoethanol, 5 mM EDTA, 25 (M theophylline, 0.5% BSA, 25 mM MgCl$_2$, 20 mM cAMP, 400 cpm/(1 [$^3$H] cAMP, 33 mM phosphocreatine, 1.67 (M GTP, 5 (Ci $^{32}$P-ATP/assay tube. The reaction mixture was incubated at 30° C. for 20 minutes and the reaction was stopped by the addition of 750 (1 of 1.5% SDS. To monitor the recovery from the column, $^3$H-labelled c-AMP was used. Cyclic-AMP was separated from ATP by passing through Dowex and alumina columns. Radioactivity was counted by scintillation counter.

The protein concentrations of the membranes used were measured by Bradford, *Anal. Biochem.* 73:248 (1976), with BSA as a standard.

Membranes from untransfected HEK-293 cells were used as a control. The enzyme expressed by this cDNA was found to be active.

EXAMPLE 4

Tissue Distribution of the Human Type IX Adenylyl Cyclase

In order to determine the tissue distribution of hAC9, Northern blotting was performed using mRNA from various tissues. Messenger RNA was purified using guanidium sodium and oligo-dT columns from various human tissues (pancreas, kidney, skeletal muscle, liver, lung, placenta, brain and heart). 2 μg of mRNA were used for each assay (per lane of blot).

The blot was pre-hybridized in a solution containing 500 mM NaHPO$_4$ (pH 7.2), 7% SDS, 1 mM EDTA (pH 8) and 1 mg/ml BSA at 65° C. for 12 hours before the addition of a probe. The entire 6.5 kb cDNA fragment from the adenylyl cyclase cDNA clone #47 was used as a probe, which was made by random primer method with $^{32}$P-dCT. Hybridization was performed at 65° C. for 16 hours followed by washing under increasingly stringent conditions. The blot was then autoradiographed.

The results of the Northern blot analysis indicated that hAC9 is an ubiquitous isoform, being expressed in all tissues tested.

All references cited and mentioned above, including patents, journal articles and texts, are all incorporated by reference herein, whether expressly incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method for identifying a candidate compound which binds to a polypeptide selected from the group consisting of:
   a) a polypeptide comprising the amino acid sequence of SEQ ID NO:2;
   b) a polypeptide encoded by the nucleotide sequence set forth in SEQ ID NO: 1; and
   c) a polypeptide encoded by nucleotides 17-3898 of the nucleotide sequence set forth in SEQ ID NO:1;
the method comprising:
   i) recombinantly producing the polypeptide;
   ii) contacting a sample comprising the polypeptide with a test compound under conditions suitable for binding; and
   iii) detecting binding of the test compound to the polypeptide; thereby identifying a compound which binds to the polypeptide.

2. The method of claim 1, wherein the polypeptide further comprises a hexa-histidine tag.

3. The method of claim 1, wherein the sample is an isolated polypeptide, a membrane-bound form of an isolated polypeptide or a cell comprising the polypeptide.

4. The method of claim 3, wherein the cell is a mammalian cell.

5. The method of claim 1, wherein the binding of the test compound to the polypeptide is detected by a method selected from the group consisting of:
   a) direct detection of test compound/polypeptide binding;
   b) a competition binding assay, wherein a candidate antagonist competes for binding to the polypeptide with either a labeled agonist or antagonist; and
   c) an immunoassay.

6. The method of claim 1, wherein the binding of the test compound to the polypeptide is detected by an assay for an activity of the polypeptide.

7. The method of claim 6, wherein the assay for activity is selected from the group consisting of:
   a) an assay for measuring adenylyl cyclase activity; and
   b) an assay for measuring the conversion of ATP to cAMP.

* * * * *